US006122546A

United States Patent [19]
Sholder et al.

[11] Patent Number: 6,122,546
[45] Date of Patent: *Sep. 19, 2000

[54] PACEMAKER AND METHOD OF OPERATING SAME THAT PROVIDES FUNCTIONAL ATRIAL CARDIAC PACING WITH VENTRICULAR SUPPORT

[75] Inventors: Jason A. Sholder, Beverly Hills; Paul A. Levine, Newhall; Joseph J. Florio, Sunland; Gene A. Bornzin, Simi Valley, all of Calif.

[73] Assignee: Pacesetter, Inc., Sylmar, Calif.

[*] Notice: This patent is subject to a terminal disclaimer.

[21] Appl. No.: 09/128,284

[22] Filed: Aug. 3, 1998

Related U.S. Application Data

[60] Division of application No. 08/854,797, May 12, 1997, Pat. No. 5,814,077, which is a continuation-in-part of application No. 08/440,599, May 15, 1995, Pat. No. 5,741,308, which is a continuation-in-part of application No. 08/225,226, Apr. 8, 1994, abandoned, which is a continuation-in-part of application No. 08/219,065, Mar. 29, 1994, abandoned, which is a continuation-in-part of application No. 07/976,153, Nov. 13, 1992, Pat. No. 5,334,220.

[51] Int. Cl.[7] ................................................. A61N 1/362
[52] U.S. Cl. ................................................................ 607/9
[58] Field of Search ..................................................... 607/9

[56] References Cited

U.S. PATENT DOCUMENTS

| 4,467,810 | 8/1984 | Vollmann ................................. 128/419 |
| 4,485,818 | 12/1984 | Leckrone et al. ......................... 128/419 |
| 4,503,858 | 3/1985 | Markowitz et al. ...................... 128/419 |
| 4,539,991 | 9/1985 | Boute et al. .............................. 128/419 |
| 4,554,920 | 11/1985 | Baker et al. .............................. 128/419 |
| 4,554,921 | 11/1985 | Boute et al. .............................. 128/419 |
| 4,559,947 | 12/1985 | Renger et al. ............................ 128/419 |
| 4,561,442 | 12/1985 | Vollmann et al. ........................ 128/419 |
| 4,562,841 | 1/1986 | Brockway et al. ....................... 128/419 |
| 4,572,193 | 2/1986 | Mann et al. .............................. 128/419 |
| 4,577,633 | 3/1986 | Berkovits et al. ........................ 128/419 |
| 4,712,555 | 12/1987 | Thornander et al. .................... 128/419 |

(List continued on next page.)

FOREIGN PATENT DOCUMENTS 2141347  12/1984  United Kingdom .

OTHER PUBLICATIONS

Rosenqvist, et al., "Relative Importance of Activation Sequence Compared to Atrioventricular Synchrony in Left Ventricular Function", *The American Journal of Cardiology*, 67, pp. 148–156 (Jan. 15, 1991).

(List continued on next page.)

*Primary Examiner*—William E. Kamm

[57] ABSTRACT

A special type of AV/PV hysteresis is provided in a dual-chamber pacemaker. A long AV delay is initially provided, thereby affording as much opportunity as possible for natural AV conduction to occur. Such long AV delay is automatically shortened should AV block occur. Periodic scanning for the return of AV conduction (absence of AV block) is performed so that the AV delay can be returned to its long value as soon as possible. In one embodiment, the pacemaker "learns" the natural conduction time (AR interval) of the patient and thereafter uses such learned natural conduction time as a reference against which subsequently measured AR intervals are compared to better distinguish conducted ventricular contractions from ectopic, pathologic, or other nonconducted ventricular contractions (e.g., PVC's). If the measured AR interval is approximately the same as the "learned" AR interval, then the R-wave at the conclusion of the measured AR interval is presumed to be a conducted R-wave that signals the return of AV conduction, and the AV delay is lengthened back to its original value. If, on the other hand, the measured AR interval is significantly different than the "learned" natural conduction time, then the R-wave at the conclusion of the measured AR interval is presumed to be a nonconducted R-wave, and the AV delay is kept short. In other embodiments, other techniques are used to distinguish a conducted R-wave from a nonconducted R-wave.

12 Claims, 6 Drawing Sheets

U.S. PATENT DOCUMENTS

| | | | |
|---|---|---|---|
| 4,712,556 | 12/1987 | Baker | 128/419 |
| 4,719,921 | 1/1988 | Chirife | 128/419 |
| 4,726,380 | 2/1988 | Vollmann et al. | 128/419 |
| 4,788,980 | 12/1988 | Mann et al. | 128/419 |
| 4,809,697 | 3/1989 | Causey et al. | 128/419 |
| 4,815,469 | 3/1989 | Cohen et al. | 128/634 |
| 4,847,617 | 7/1989 | Silvian | 340/870 |
| 4,872,459 | 10/1989 | Pless et al. | 128/419 |
| 4,875,483 | 10/1989 | Vollmann et al. | 128/419 |
| 4,880,005 | 11/1989 | Pless et al. | 128/419 |
| 4,940,052 | 7/1990 | Mann et al. | 128/419 |
| 4,940,053 | 7/1990 | Mann et al. | 128/419 |
| 4,944,298 | 7/1990 | Sholder | 128/419 |
| 4,974,589 | 12/1990 | Sholder | 128/419 |
| 5,016,630 | 5/1991 | Moberg | 128/419 |
| 5,040,534 | 8/1991 | Mann et al. | 128/419 |
| 5,044,365 | 9/1991 | Webb et al. | 128/419 |
| 5,063,927 | 11/1991 | Webb et al. | 128/419 |
| 5,133,350 | 7/1992 | Duffin | 128/419 |
| 5,144,950 | 9/1992 | Stoop et al. | 128/419 |
| 5,237,992 | 8/1993 | Poore | 128/419 |
| 5,269,299 | 12/1993 | Duncan | 128/419 |
| 5,334,220 | 8/1994 | Sholder | 607/9 |
| 5,340,361 | 8/1994 | Sholder | 607/24 |
| 5,814,077 | 9/1998 | Sholder | 607/9 |

OTHER PUBLICATIONS

Askenazi, et al., "Alteration of Left Ventricular Performance by Left Bundle Branch Block Simulated with Atrioventricular Sequential Pacing", *The American Journal of Cardiology*, 53, pp. 99–104 (Jan. 1, 1984).

"Journal of the American College of Cardiology", *Abstracts of Original Contributions, 41st Annual Scientific Session, American College of Cardiology, Dallas Texas*, (Apr. 12–16, 1992).

Karpawich, et al., "Developmental sequelae of fixed–rate ventricular pacing in the immature canine heart: An electrophysiologic, hemodynamic, and histopathologic evaluation", *American Heart Journal*, 119:5; pp. 1077–1083 (May 1990).

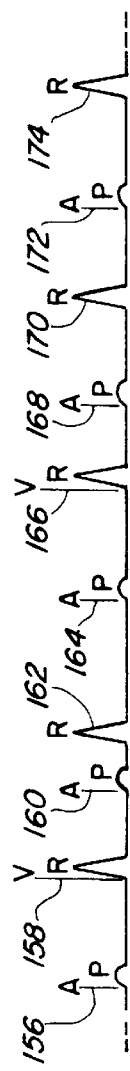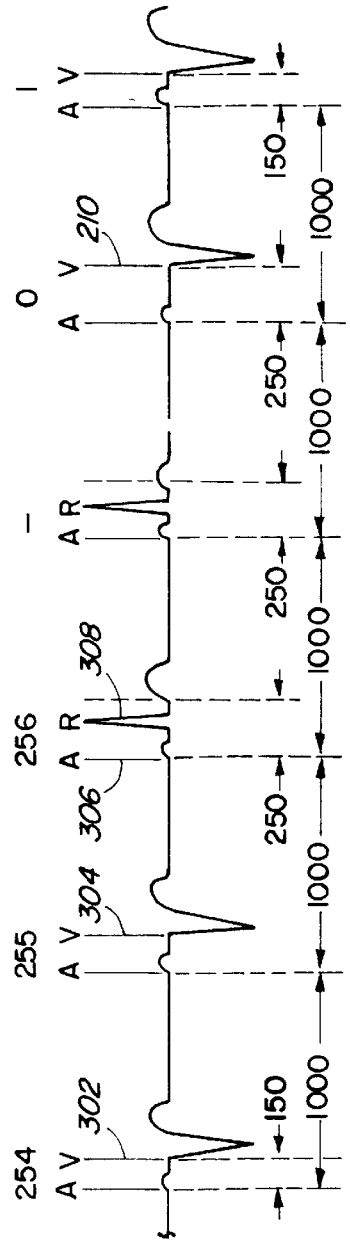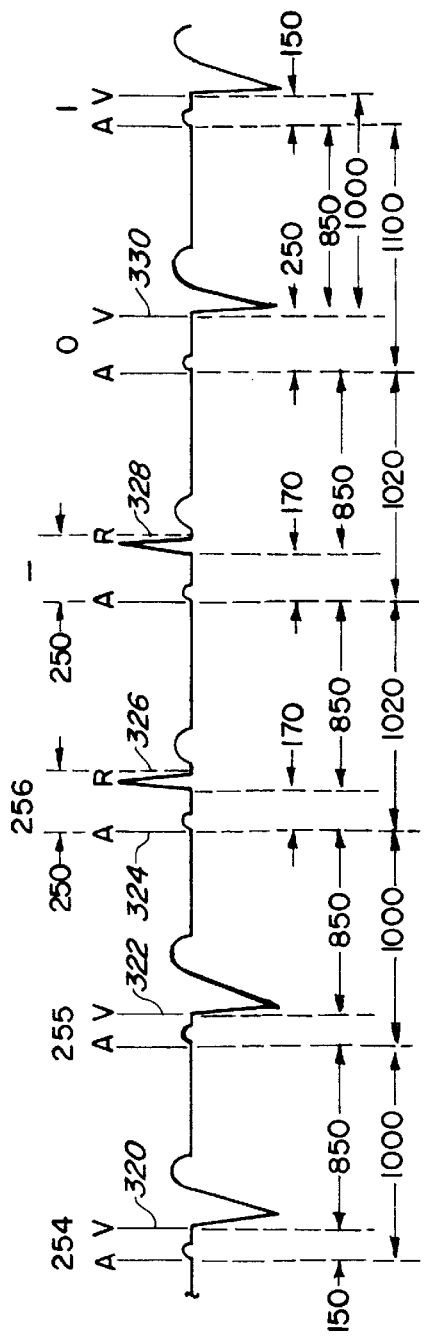
Fig. 9
Fig. 13
Fig. 14

PACEMAKER AND METHOD OF OPERATING SAME THAT PROVIDES FUNCTIONAL ATRIAL CARDIAC PACING WITH VENTRICULAR SUPPORT

CROSS-REFERENCE TO RELATED APPLICATIONS

This application is division of a prior application Ser. No. 08/854,797, filed May 12, 1997 (now U.S. Pat. No. 5,814,077, issued Sep. 29, 1998), which is a a continuation-in-part of application Ser. No. 08/440,599, filed May 15, 1995 now U.S. Pat. No. 5,471,308; which is a continuation-in-part of application Ser. No. 08/225,226, filed Apr. 8, 1994, now abandoned; which is a continuation-in-part of application Ser. No. 08/219,065, filed Mar. 29, 1994, now abandoned; which is a continuation-in-part Ser. No. 07/976,153 now U.S. Pat. No. 5,334,220, issued Aug. 2, 1994; which applications and patent are incorporated herein by reference.

FIELD OF THE INVENTION

The present invention relates to implantable medical devices and methods, and more particularly, to an implantable dual-chamber pacemaker that provides AAI pacing with back-up ventricular support to improve cardiac hemodynamics. Even more particularly, the invention provides a dual-chamber pacemaker, and method of operating such pacemaker, wherein a type of positive atrioventricular (AV) hysteresis is employed that provides a long AV delay, or AV interval (AVI), thereby affording as much opportunity as possible for natural cardiac conduction to occur, but where the AVI is automatically shortened during AV block. Further, the invention periodically scans or searches for a return of AV conduction (absence of AV block) so that the AVI can be returned to its longer value as soon as possible. To assist with determining when AV conduction has returned, the invention further provides several different ways to differentiate between those ventricular depolarizations (R-waves) that evidence the return of AV conduction from those that do not.

In the above-identified patent and applications, of which this application is a continuation-in-part, there is disclosed an implantable dual-chamber pacemaker that automatically sets its AVI to a value that is a prescribed amount less than or greater than a measured natural conduction time of a patient within whom the pacemaker is implanted. In the present application, the AVI is set to a long or short value depending upon whether AV conduction is present or not. In determining whether AV conduction is present or not, the implantable pacemaker circuits monitor those ventricular contractions that normally signal the end of the natural conduction time to determine if such contractions truly evidence a return of AV conduction or not. One way this is done, for example, is to monitor and "learn" the natural conduction time of the patient's heart, and thereafter use such learned natural conduction time to better distinguish naturally, conducted ventricular contractions (which signal the return of AV conduction, and hence signal that the AVI can be lengthened) from ectopic or pathologic ventricular contractions (which do not signal the return of AV conduction, and hence which suggest that the AVI should be kept short).

BACKGROUND OF THE INVENTION

For a thorough background description of the physiology of a human heart, as well as a description of the basic operation of an implantable pacemaker, reference should be made to the various patents and patent applications cited herein. That which is presented below is a brief summary of such background information.

As is known in the art, the basic function of the heart is to pump (circulate) blood throughout the body thereby delivering oxygen and nutrients to the various tissues and removing waste products and carbon dioxide therefrom. The heart is divided into four chambers comprised of two atria and two ventricles. The atria are the collecting chambers holding the blood that returns to the heart until the ventricles are ready to receive this blood. The ventricles are the primary pumping chambers. The pumping function of the heart is achieved by a coordinated contraction of the muscular walls of the atria and the ventricles.

As is also known in the art, the atria are more than simple collecting chambers. The atria contain the heart's own spontaneous pacemaker, the sinus node, that controls the rate at which the heartbeats or contracts. Furthermore, atrial contraction helps to fill the ventricles, contributing to optimal filling of the ventricles, thus maximizing the amount of blood that the heart is able to pump with each contraction, i.e., maximizing the hemodynamic efficiency of the heart. In the normal heart, an atrial contraction is followed, after a short period of time (normally 120 to 200 ms), by a ventricular contraction, i.e., a conducted R-wave.

The period of cardiac contraction during which the heart actively ejects the blood into the arterial blood vessels is called systole. The period of cardiac relaxation during which the chambers are being filled with blood is called diastole. Atrial and ventricular systole are sequenced allowing the atrial contraction to help optimally fill the ventricle. This sequencing is termed AV synchrony.

A cardiac cycle (or heartbeat) comprises one sequence of systole and diastole. It can be detected by a physician counting the patient's pulse rate. It is also reflected by the cardiac rhythm as recorded on an electrocardiogram. The electrocardiogram (ECG) records the electrical activity of the heart as seen on the surface of the body. The electrical activity corresponds to the electrical cardiac depolarization in either the atrium and/or ventricle. On the ECG, the atrial depolarization is represented by a waveform referred to as the P-wave, while the ventricular depolarization is represented by a waveform referred to as the QRS complex, sometimes abbreviated as an "R-wave." A normal heart rate varies between 60 to 100 heartbeats (or cardiac cycles) per minute with an average of 72 bpm resulting in approximately 100,000 cardiac cycles per day. The heart rate normally increases during periods of stress (physical or emotional) and slows during periods of rest (sleep).

The amount of blood that the heart pumps in one minute is called the cardiac output. It is calculated by the amount of blood ejected with each heartbeat (stroke volume) multiplied by the number of heartbeats in a minute. If the heart rate is too slow to meet the physiological requirements of the body, the cardiac output will not be sufficient to meet the metabolic demands of the body. One of two major symptoms may result. If the heart effectively stops with no heartbeat, there will be no blood flow and if this is sustained for a critical period of time (10 to 30 seconds), the individual will faint. If there is a heartbeat but it is too slow, the patient will be tired and weak (termed low cardiac output).

Too slow a heartbeat is termed a bradycardia. Any heart rate below a rate of 60 bpm is considered a bradycardia, however bradycardia only needs to be treated if it is a persistent abnormality and causes a patient to have symptoms. In such cases, implantation of a permanent electronic pacemaker is often prescribed.

An electronic pacemaker may also be referred to as a pacing system, or a cardiac pacemaker. The pacing system is comprised of two major components. One component is a pulse generator that includes electronic circuitry and a power cell or battery. The other is a lead or leads which connect the pulse generator to the heart.

Electronic pacemakers are described as either single-chamber or dual-chamber systems. A single-chamber system stimulates and senses the same chamber of the heart (atrium or ventricle). A dual-chamber system stimulates and/or senses in both chambers of the heart (atrium and ventricle). The electronic pacemaker delivers an electrical stimulus to stimulate the heart to contract when the patient's own spontaneous pacemaker (i.e., the sinus node) fails or when conduction of an R-wave is blocked. In this way, the electronic pacemaker can help to stabilize the heart rate of a patient's heart.

Conduction of an R-wave can be blocked in a variety of ways. For example, the atrio-ventricular (AV) node may be partially or completely insensitive to the propagation of a P-wave. Alternately, the Bundle of His or a bundle branch may suddenly stop propagation of the R-wave to the ventricular tissue. Hereinafter, a P-wave which originates in the sinus node shall be referred to as a "spontaneous P-wave," a naturally occurring R-wave which is triggered by either a spontaneous or paced P-wave shall be referred to as a "conducted R-wave," and the AV node, the Bundle of His, etc. shall be referred to as the heart's "conduction system."

Most pacemakers are referred to as demand-type pacemakers. This means that they are capable of sensing the electrical signal in or on the cardiac chamber by way of the pacing lead, which is placed in or on the chamber. The electrical signal as recorded in or on the heart is called an electrogram (EGM), or sometimes an intracardiac electrogram (IEGM), and is a relatively large signal with very rapid changes in electrical potential. The most rapid portion of this signal is called the intrinsic deflection (ID), which is what is sensed by the pacemaker. Although medical personnel commonly talk about pacemakers sensing P-waves or R-waves, this is not technically correct. The P-wave and R-wave, technically, are recorded from the surface of the body. The pacemaker, in contrast, senses the atrial or ventricular intrinsic deflection (ID) portion of the atrial or ventricular electrogram from within the heart. The atrial EGM coincides with the P-wave of the surface ECG while the ventricular EGM coincides with the R-wave of the surface ECG. Thus, the terms P-wave and R-wave are commonly used, and will be used herein, synonymously with the atrial and ventricular intrinsic deflection portions of the atrial and ventricular electrograms.

One of the parameters of the pacemaker that can commonly be programmed or set by the physician is a base rate, which is the lowest heart rate that can be detected in a patient before the pacemaker will begin pacing. If the patient's ventricular heart rate is faster than this base rate, the pacemaker will recognize the ventricular electrical depolarization and be either inhibited or triggered depending upon how the electronic pacemaker is configured (and will reset its various timing cycles). If the patient's ventricular heart rate slows below the base rate of the electronic pacemaker, the electronic pacemaker's timers will expire (or "time out") and will cause the electronic pacemaker to periodically release an output pulse (electrical stimulation) at the base rate, thus preventing the patient's ventricular heart rate from falling below the base rate.

The interval between consecutive output pulses within the same chamber is termed the automatic interval or basic pacing interval. The interval between a sensed event and the ensuing paced event is called an escape interval. In single-chamber pacing systems, the automatic and escape intervals are commonly identical. In dual-chamber pacing systems, the basic pacing interval is divided into two sub-intervals. The interval from a sensed R-wave or ventricular paced event to the atrial paced event is called an atrial escape interval. The interval from the sensed P-wave or atrial paced event to the ventricular paced event is called the AV interval (AVI), or AV delay.

In the majority of individuals, the most effective heartbeat is triggered by the patient's own spontaneous pacemaker. The electronic pacemaker is intended to fill in when the patient's spontaneous pacemaker fails or when the heart's conduction system fails. The first pacing mode that was developed was single-chamber ventricular stimulation. It was soon recognized that this resulted in the loss of appropriate synchronization between the atria and ventricles in which case, the hemodynamic efficiency of the heart was compromised and the cardiac output fell despite maintaining an adequate rate. In those patient's whose need for a pacemaker was intermittent, with a normal rhythm occurring between times when pacing support was required, electronic pacemakers were developed which were set to a slow base rate. This allowed the patient's underlying rhythm to slow to this very low base rate before the electronic pacemaker would be activated. While the patient would be protected from asystole (a total absence of any heartbeat), the loss of appropriate AV synchrony combined with the slow rate was often hemodynamically inefficient, i.e., the efficiency of the heart as a pump was compromised.

One approach to remedying this inefficiency utilizes a hysteresis circuit, in which the hysteresis escape rate of the pacemaker is slower than the automatic rate. When the hysteresis circuit was invoked, the patient's underlying cardiac rhythm is permitted to persist until the heart rate falls below a hysteresis escape rate. When this happens, there is one cycle of pacing at the hysteresis escape rate followed by pacing at a more rapid rate until a conducted R-wave is sensed. When the conducted R-wave is sensed, the hysteresis escape rate is restored to again inhibit the pacemaker and allow underlying cardiac rhythm to persist.

A number of heretofore unsolved problems exist with hysteresis. One problem is confusion on the part of the medical personnel caring for the patient as to why the patient's underlying rhythm occurs at a slower rate than the automatic rate to which the pacemaker is set. A second problem is that the slow atrial escape rate promotes the occurrence of premature ventricular contractions (PVC's), ectopic beats, or pathologic R-waves. In operation, the electronic circuits of the pacemaker sense a PVC as an R-wave, and therefore assume that natural conduction has returned, and that therefore the pacing at the more rapid rate is no longer needed. As a result, the escape interval of the pacemaker is reset to the slower hysteresis escape rate following each PVC, thereby effectively maintaining a slower cardiac rate.

In view of the above problems, (confusion on the part of the medical community, and the repeated resetting of the pacemaker to a slower rate by the occurrence of PVC's) hysteresis was not well accepted by the medical community until such time as it was introduced as a programmable parameter capable of being enabled or disabled, and when enabled, capable of being adjusted so that the degree of hysteresis (i.e., the difference between the slow and fast atrial escape rates) could be changed.

Since the goal of hysteresis is to allow the patient's underlying rhythm with appropriate AV synchrony for as much time as possible, while providing pacing support at a hemodynamically efficient rate at only those times when the patient requires such support, hysteresis was not incorporated into the first dual-chamber pacing systems, which were designed to always provide hemodynamically efficient AV synchrony. Some physicians, however, recognized that some patients, whose heart rate precipitously and abruptly slowed, not only needed a more rapid cardiac rate at these times, but they also required AV synchrony. Problematically, if the base rate of the typical dual-chamber pacemaker is programmed to a rate required when cardiac pacing is needed by such patients, the electronic pacemaker frequently controls the patient's rhythm even when cardiac pacing is not needed. In an attempt to solve this problem, adaptations were introduced into some of the first generation dual-chamber electronic pacemakers to allow hysteresis in the DDI mode. This allowed the electronic pacemaker to remain inhibited in the presence of sensed cardiac signals, and to stimulate only when the electronic pacemaker was needed. Once activated, the electronic pacemaker will then pace in both atrium and ventricle while tracking at the atrial rate until such time as an R-wave was sensed, thereby inhibiting the generation of a V-pulse. Once inhibited, hysteresis would required expiration of the hysteresis escape interval before the electronic pacemaker again released output pulses.

Several problems persist in the application of hysteresis in the DDI mode. The first is that PVC's, a limitation first noted with single-chamber hysteresis systems, may be equally limiting in the dual-chamber pacing mode. The second is that when pacing is required, patients often need a relatively short AV interval for optimum hemodynamic function. However, setting a short AV interval could result in the pacemaker usurping control of the heart's normal conduction system, resulting in sustained periods of pacing when it is no longer required. On the other hand, setting a long AV interval, while resulting in appropriate pacing system inhibition when pacing therapy is not required, may allow AV conduction when pacing is required, causing repeated reinitiation of the longer hysteresis escape interval. Consequently, sustained pacing at the relatively slow hysteresis escape rate may result, which (while appropriate for a few cardiac cycles) may not be appropriate for sustained periods of pacing. An electronic pacemaker that overcomes these problems would be highly desirable.

An additional problem exists when hysteresis is utilized in an AAI(R) mode of operation, namely, AAI(R) pacemaker syndrome. AAI(R) pacemaker syndrome exists when the heart rate (i.e., atrial paced rate) increases or an A-A interval shortens (whether due to the programmed automatic rate or under rate responsive sensor drive), but the A-R interval does not shorten. As a result, an atrial output pulse (A-pulse), which causes an atrial contraction, is generated coincident with the preceding conducted ventricular contraction (R-wave). When this occurs, the atrium contracts against a closed A-V valve, and therefore, is unable to force blood into the ventricle (which is also contracting). As a result, poor hemodynamic efficiency is achieved.

From the above, it is evident that improvements in the use of hysteresis in dual-chamber pacemakers are needed and desirable.

SUMMARY OF THE INVENTION

The present invention addresses the above and other needs by providing a special type of AV/PV hysteresis in a dual-chamber pacemaker wherein a long AV delay (or AVI) is provided, thereby affording as much opportunity as possible for natural AV conduction to occur, but where the AV delay is automatically shortened during Av block. Once the AV delay is automatically shortened, the invention periodically searches for a return of AV conduction (absence of AV block) so that the AV delay can be returned to its longer value as soon as possible, thereby optimizing hemodynamic efficiency.

In accordance with one aspect of the invention, the pacemaker circuits determine or "learn" the natural conduction time of the patient. This is done by monitoring or measuring the "AR interval" (where the AR interval is the time interval between an atrial event, either a P-wave or an A-pulse, and a subsequently conducted R-wave) over a specified period of time. Once learned, the natural conduction time is used as a reference against which subsequently measured AR intervals are compared to better distinguish conducted ventricular contractions from ectopic, pathologic, or other nonconducted ventricular contractions (e.g., PvC's). If the measured AR interval is approximately the same as the "learned" natural conduction time, then the R-wave at the conclusion of the measured AR interval is presumed to be a conducted R-wave that signals the return of AV conduction. Once AV conduction returns, in accordance with the AV/PV hysteresis system employed by the invention, the AV delay is lengthened to its original value. If, on the other hand, the measured AR interval is significantly different than the "learned" natural conduction time, then the R-wave at the conclusion of the measured AR interval is presumed to be a norconducted R-wave, and the AV delay is kept short.

In accordance with other aspects of the invention, other techniques may be used to verify the return of AV conduction, in stead of, or in addition to, the monitoring or "learning" of the natural conduction time (AR interval) as described above. Such other techniques include, e.g., defining a programmable time window within the cardiac cycle that defines when an R-wave that occurs during the cardiac cycle is one that evidences the return of AV conduction; measuring the amplitude of a sensed R-wave to determine if such amplitude evidences the return of AV conduction; examining the morphology (shape) of a sensed R-wave to determine if it is indicative of the return of AV conduction; and/or requiring two or three or more consecutive occurrences of an R-wave during consecutive cardiac cycles before making a decision as to whether AV conduction has returned. Indeed, any technique that aids in identifying whether AV conduction is present or absent may be used with the invention.

In the above manner, the benefits of hysteresis pacing are achieved, while at the same time the problems that have plagued prior art hysteresis systems are minimized. For example, the continual resetting of the AV delay to its longer value, caused by PVC's, or other nonconducted ventricular contractions, as commonly occur in patients fitted with electronic pacemakers, is avoided. This is because only an R-wave at the conclusion of a measured AR interval that matches a "learned" natural conduction time, or that otherwise evidences the return of AV conduction, allows the AV delay to be reset back to its longer value in the dual-chamber pacing system when programmed to a long AV delay.

In accordance with another aspect of the invention, for use with pacemakers having rate-responsive features, the amount by which the AV delay or AVI is changed may be keyed to the sensor-indicated rate of the pacemaker. This effectively prevents the AAI(R) pacemaker syndrome from occurring.

It is thus a feature of the present invention to provide an implantable pacemaker that automatically sets its AV interval to either a long or short value in order to optimize the hemodynamic performance of the heart with which the pacemaker is used.

It is another feature of the invention to provide such setting of the AV interval while avoiding the AAI(R) pacemaker syndrome, i.e., preventing the issuance of an A-pulse on top of an R-wave (including the S-T and the T-waves), thereby assuring that the atria do not contract at a time when the atrial-ventricular valves are closed.

It is yet another feature of the invention to provide an automatic AV shortening procedure. Such procedure may be automatically invoked to shorten the AV interval (e.g., whenever AV block occurs), and may thereafter automatically search for the return of AV conduction (e.g., whenever a conducted R-wave is sensed). Alternatively, such searching may occur in accordance with a prescribed schedule (e.g., every x cardiac cycles, where x is an integer greater than eight), or pursuant to some other defined schedule. Once AV conduction returns, the AV interval is then reset to its original (longer) value.

It is an additional feature of the invention to provide positive AV hysteresis within a dual-chamber pacemaker wherein several different techniques may be used to verify the presence or absence of AV conduction, and therefore to signal when the AV interval should be switched between a short value and a longer value.

It is still another feature of the invention, in accordance with one embodiment thereof, to provide a atrial-based dual-chamber pacemaker, and method of operating such pacemaker, wherein the overall A-to-A interval of the pacemaker remains unchanged even through the AV interval does change between long and short values.

It is another feature of the invention to provide ventricular support in a dual-chambered pacemaker operating in an AAI mode only when it is needed (i.e., only when AV block is detected), so as to minimize unnecessary power consumption by the cardiac pacemaker, and to terminate the ventricular support response when there is AV conduction.

BRIEF DESCRIPTION OF THE DRAWINGS

The above and other aspects, features and advantages of the present invention will be more apparent from the following more particular description thereof, presented in conjunction with the following drawings wherein:

FIG. 9 depicts an exemplary timing/waveform diagram as in FIGS. 2–4 that depicts the cardiac and pacemaker events that transpire as the pacemaker of FIG. 1 utilizes the average AR interval learned in FIG. 8 to distinguish between, e.g., premature ventricular contractions and conducted ventricular contractions;

FIG. 13 is a timing/waveform diagram that depicts a specific example of positive AV hysteresis with atrial based timing in accordance with the present invention; and FIG. 14 is a timing/waveform diagram that depicts a specific example of positive AV hysteresis with ventricular-based timing in accordance with the present invention.

Corresponding reference characters indicate corresponding components throughout the several views of the drawings.

DETAILED DESCRIPTION OF THE INVENTION

Figure 1:
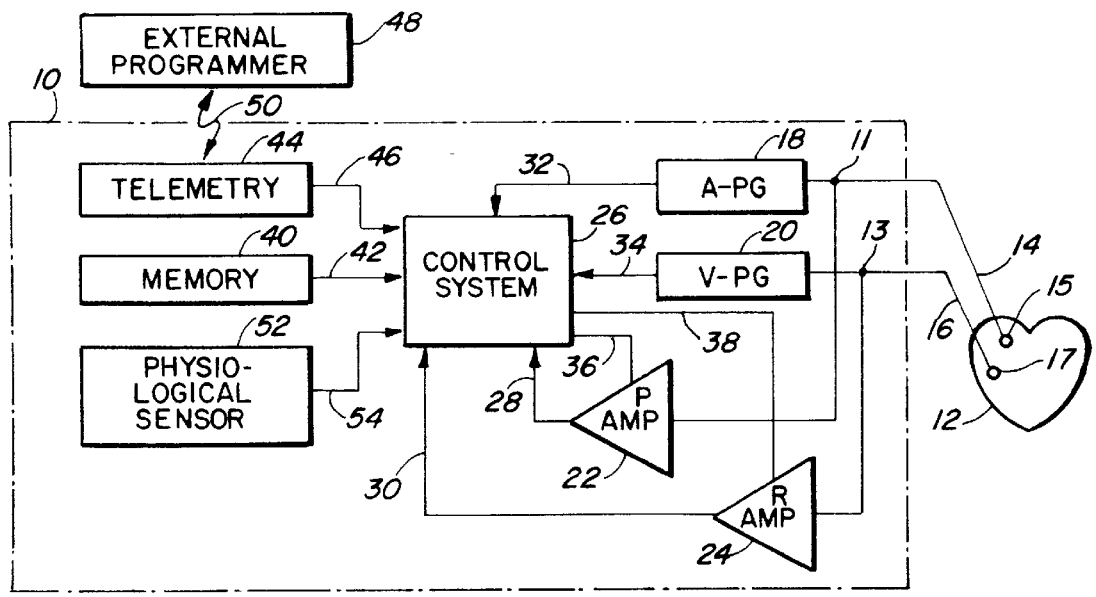
FIG. 1 is a block diagram of an electronic dual-chamber electronic pacemaker capable of operating in accordance with the invention.

The following description is of the best mode presently contemplated for carrying out the invention. This description is not to be taken in a limiting sense, but is made merely for the purpose of describing the general principles of the invention. The scope of the invention should be determined with reference to the claims.

As indicated above, the present invention is directed to method of operating an implantable dual-chamber pacemaker that automatically sets or adjusts the AV interval (or PV interval) of the pacemaker to a long value or a short value, thereby providing a type of dual-chamber hysteresis. If AV conduction is present (i e., if a conducted contraction of the ventricle is sensed, as evidenced by the presence of an R-wave which regularly follows an atrial contraction, either a spontaneous P-wave or a paced atrial contraction), then the longer AV (or PV) interval is used, thereby preserving the natural hemodynamics of the heart and conserving the limited energy of the pacemaker's battery. If AV block exists (as determined by the lack of an R-wave during the longer AV interval), then a V-pulse is generated to pace the ventricle, and the shorter AV interval is used thereafter.

On a regular basis (e.g., after a fixed period of time or a fixed number of cardiac cycles), a determination is made as to whether AV conduction has returned. If AV conduction has returned, the longer AV interval is again reinstated. If AV block persists, then the shorter AV interval continues to be used. In a rate-responsive pacemaker, both the longer and shorter AV intervals may be keyed to the sensor-indicated rate, i.e., these values change proportionate to the change in the sensor-indicated rate, so as to avoid the occurrence of the AAI(R) pacemaker syndrome.

Throughout the discussion that follows, reference will frequently be made to the AV interval ("AVI"). It is to be understood that all such references to the AV interval also apply to the PV interval, and that whether the AV or PV interval is used depends upon the particular type of atrial activity—an A-pulse or a P-wave—that starts the AV (or PV) interval. Similarly, it is to be understood that any references made to the PV interval also apply to the AV interval. It is further to be understood that when the PV interval is used, it will typically be (but does not have to be) shorter than the AV interval by a prescribed amount, e.g., 20–40 msec, to account for the latency time involved between applying an A-pulse and having the atrial tissue respond with a depolarization. Those of skill in the art can readily fashion appropriate circuitry to utilize either an AV interval or a PV interval, whichever applies to a given cardiac cycle. For the discussion that follows, then, where reference is made to the AV interval, such AV interval should be considered as the time interval between atrial channel activity, whether such atrial channel activity comprises an A-pulse or a P-wave, and the subsequent delivery of a ventricular stimulation pulse (V-pulse).

Advantageously, the present invention may be implemented using a wide variety of dual-chamber pacemaker configurations and pacemaker hardware. Any pacemaker configuration that allows the pacemaker AV (or PV) interval to be automatically set to a desired value (e.g., a long value or a short value) may be used to implement the invention. The descriptions that follow are only exemplary of a few of such configurations.

In FIG. 1, there is illustrated a functional block diagram of a dual-chamber pacemaker 10. Such functional diagram will be used to teach the primary functions carried out by the pacemaker 10. A preferred embodiment of the actual hardware and components used within the pacemaker 10 to carry out the pacemaker functions will then be described in conjunction with FIGS. 10–12. Next, techniques or methods that may be used by the pacemaker 10 to implement the present invention will be described in conjunction with the flow diagrams and timing/event diagrams of FIGS. 2–9.

As shown in FIG. 1, the pacemaker 10 is coupled to a heart 12 by way of leads 14 and 16. (Note, in subsequent figures, e.g., FIG. 10, the leads 14 and 16 are referred to as the lead system 19.) The lead 14 has an electrode 15 that is in contact with one of the atria of the heart, and the lead 16 has an electrode 17 that is in contact with one of the ventricles of the heart. The leads 14 and 16 carry stimulating pulses to the electrodes 15 and 17 from an atrial pulse generator (A-PG) 18 and a ventricular pulse generator (V-PG) 20, respectively. Further, electrical signals from the atria are carried from the electrode 15, through the lead 14, to the input terminal of an atrial channel sense amplifier (P-AMP) 22; and electrical signals from the ventricles are carried from the electrode 17, through the lead 16, to the input terminal of a ventricular sense channel amplifier (R-AMP) 24.

Controlling the dual-chamber pacemaker 10 is a control circuit or control system 26. The control system 26 receives the output signals from the atrial amplifier 22 over signal line 28. Similarly, the control system 26 receives the output signals from the ventricular amplifier 24 over signal line 30. The output signals on signal lines 28 and 30 are generated each time that a P-wave or an R-wave is sensed within the heart 12. The control circuit or system 26 also generates trigger signals that are sent to the atrial pulse generator 18 and the ventricular pulse generator 20 over signal lines 32 and 34, respectively. These trigger signals are generated each time that a stimulation pulse is to be generated by the respective pulse generator 18 or 20. A stimulation pulse generated by the A-PG 18 is referred to as the "A-pulse," and the stimulation pulse generated by the V-PG 20 is referred to as the "V-pulse." During the time that either an A-pulse or V-pulse is being delivered to the heart, the corresponding amplifier, P-AMP 22 and/or R-AMP 24, is typically disabled by way of a blanking signal presented to these amplifiers from the control system over signal lines 36 and 38, respectively. This blanking action prevents the amplifiers 22 and 24 from becoming saturated from the relatively large A-pulse or V-pulse, respectively, that is present at the input terminals of such amplifiers during this time. Such blanking action also helps prevent residual electrical signals present in the muscle tissue as a result of the pacemaker stimulation from being interpreted as P-waves or R-waves.

As shown in FIG. 1, the pacemaker 10 also includes a memory circuit 40 that is coupled to the control system 26 over a suitable data/address bus 42. The memory circuit 40 allows certain control parameters, used by the control system 26 in controlling the operation of the pacemaker, to be programmably stored and modified, as required, in order to customize the pacemaker's operation to suit the needs of a particular patient. Such data includes the basic timing intervals used during operation of the pacemaker, such as the programmed atrial escape interval (AEI). For purposes of the present invention, such data may also include a family of AV interval data that may be retrieved during an adjustment sequence of the AV interval, as explained more fully below. Further, data sensed during the operation of the pacemaker may be stored in the memory circuit 40 for later retrieval and analysis.

A telemetry circuit 44 is further included in the pacemaker 10. This telemetry circuit 44 is connected to the control system 26 by way of a suitable command/data bus 46. In turn, the telemetry circuit 44, which is included within the implantable pacemaker 10, may be selectively coupled to an external programming device 48 by means of an appropriate communication link 50, which communication link 50 may be any suitable electromagnetic link, such as an RF (radio frequency) channel. Advantageously, through the external programmer 48 and the communication link 50, desired commands may be sent to the control system 26. Similarly, through this communication link 50 and the programmer 48, data (either held within the control system 26, as in a data latch, or stored within the memory circuit 40), may be remotely received from the pacemaker 10. In this manner, noninvasive communications can be established from time to time with the implanted pacemaker 10 from a remote, non-implanted location. Many suitable telemetry circuits known in the art that may be used with the present invention for the telemetry circuit 44. See, e.g., U.S. Pat. No. 4,847, 617, incorporated herein by reference.

The pacemaker 10 in FIG. 1 is referred to as a dual-chamber pacemaker because it interfaces with both the atrial and the ventricular chamber of the heart. Those portions of the pacemaker 10 that interface with the atria, e.g., the lead 14, the P-wave sense amplifier P-AMP 22, the atrial pulse generator A-PG 18, and corresponding portions of the control system 26, are commonly referred to as the atrial channel. Similarly, those portions of the pacemaker 10 that interface with the ventricle, e.g., the lead 16, the R-wave sense amplifier R-AMP 24, the V-pulse generator V-PG 20, and corresponding portions of the control system 26, are commonly referred to as the ventricular channel.

Throughout the discussion that follows, frequent reference will be made to "atrial activity," "atrial events," "ventricular activity," or "ventricular events." Atrial activity or an atrial event thus comprises either the sensing of a P-wave by the sense amplifier P-AMP 22, or the generating of an A-pulse by the A-pulse generator A-PG 18. Similarly, ventricular activity or a ventricular event comprises either the sensing of an R-wave by the sense amplifier R-AMP 24 or the generation of a V-pulse by the V-pulse generator V-PG 20.

In some pacemakers that implement the present invention, the pacemaker 10 may further include one or more physiological sensors 52 that is/are connected to the control system 26 of the pacemaker over a suitable connection line 54. While the sensor 52 is illustrated in FIG. 1 as being included within the pacemaker 10, it is to be understood that the sensor may also be external to the pacemaker 10, yet still be implanted within or carried by the patient. A common type of sensor is an activity sensor, such as a piezoelectric crystal, mounted to the case of the pacemaker. Other types of physiologic sensors, such as sensors that sense the oxygen content of blood, respiration rate, pH of blood, body motion, and the like, may also be used in lieu of, or in addition to, an activity sensor. The type of sensor, if any, used is not critical to the present invention. Any sensor or combination of sensors capable of sensing some physiological parameter relatable to the rate at which the heart should be beating can be used. A pacemaker using such sensors is commonly referred to as a "rate-responsive" pacemaker because such a pacemaker adjusts the rate (escape interval) of the pacemaker in a manner that tracks the physiological needs of the patient. Further, such sensors, and the circuitry used therewith, generate what is usually referred to as a "sensor-indicated rate" (SIR) signal, which signal defines the minimum rate at which the heart should be beating given the physiological activity or other parameters sensed by the sensors.

Figure 10:
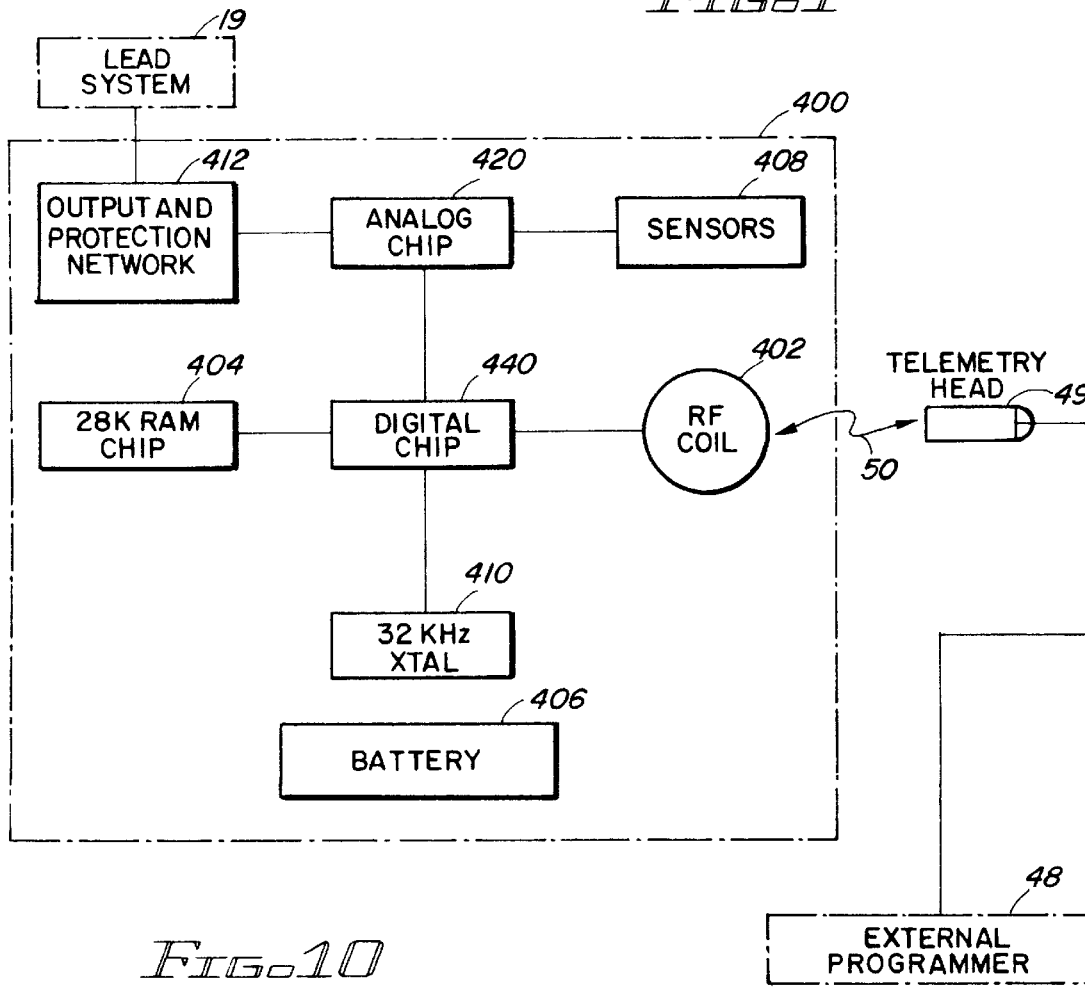
FIG. 10 is a block diagram of a pacing system that depicts, in accordance with a preferred embodiment of the invention, the main hardware components of the implantable pacemaker of FIG. 1.

Referring next to FIG. 10, there is shown a preferred configuration of a pacing system made in accordance with the present invention. The system includes the external programmer 48, the implantable pacemaker 10, and the lead system 19. The lead system 19 includes conventional atrial and ventricular leads and electrodes, as described previously. The lead system 19 may also include an oxygen sensor lead, which lead typically contains an LED-detector assembly used to measure the oxygen content of the blood. Such a lead is described, e.g., in U.S. Pat. No. 4,815,469, incorporated herein by reference.

The external programmer 48 includes a telemetry head 49 that is positioned proximate the implantable pacemaker 10 whenever the communication link 50 is to be established between the pacemaker 10 and the external programmer 48. The external programmer may be of conventional design, as described, e.g., in U.S. Pat. No. 4,809,697, incorporated herein by reference.

The components of the pacemaker 10 are housed within a suitable sealed case or housing 400 (which case or housing is represented in FIG. 10 by the dashed line 400). The case 400 is preferably a titanium metal case. The components within the case 400 include an RF coil 402, a memory chip 404, a battery 406, one or more sensors in a sensor circuit 408, a crystal 410, an output/protection network 412, an analog chip 420 and a digital chip 440.

The battery 406, which is by volume the largest component within the pacemaker 10, may be of conventional design, and is a lithium battery that provides operating power to all of the electronic circuits within the pacemaker. The RF coil 402 is used to establish the communication link 50 with the telemetry head 49. The crystal 410 is used in conjunction with a crystal oscillator circuit on the digital chip 440 (described below) to provide a stable clock frequency for the pacemaker circuits. For the embodiment shown in FIG. 10, the frequency of the crystal oscillator is 32 KHz, although any suitable frequency could be used. The sensor circuit 408 includes appropriate sensors used by the pacemaker as it carries out a rate-responsive pacing function. For example, in one embodiment, the sensor circuit 408 includes an accelerometer adapted to sense patient activity.

The memory chip 404 is a low-power static random access memory (RAM) chip wherein the operating parameters, e.g., control variables, of the pacemaker may be stored, and wherein sensed data may be stored, as required. The analog chip 420 and the digital chip 440 contain the main processing and control circuits of the pacemaker. These chips are advantageously designed to minimize the number of components needed external thereto for operation of the pacemaker. The analog chip 420 interfaces with the lead system 19 through the output and protection network 412, which network includes output capacitors, appropriate feed-through connectors to allow electrical connection through the hermetically sealed case, and the like, as are commonly used in implantable medical devices.

Figure 11:
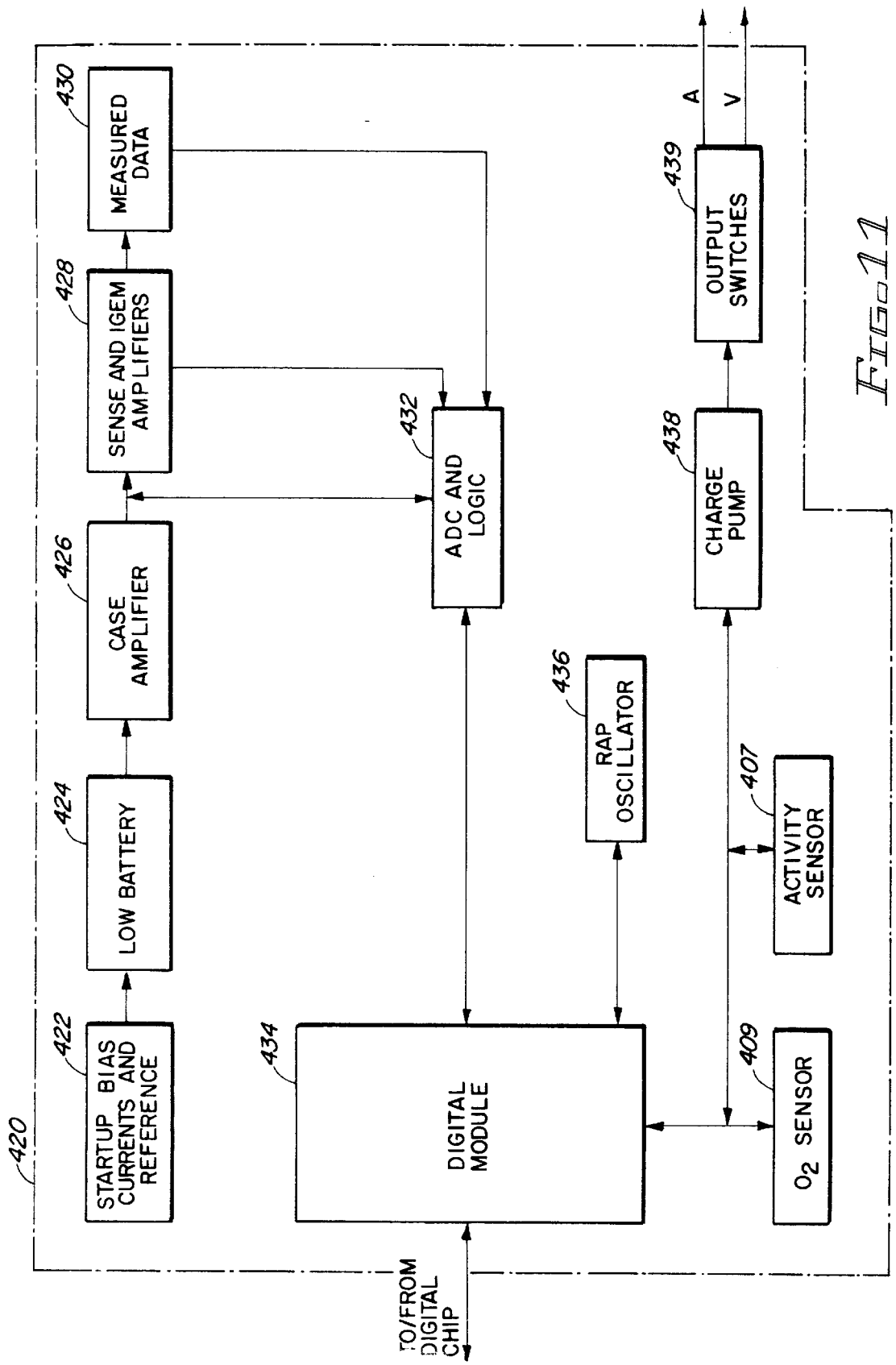
FIG. 11 is a block diagram of the analog chip portion of the pacemaker of FIG. 10.

In FIG. 11, a block diagram of the analog chip 420 is shown. The analog chip 420 contains all the necessary subsystems and modules to interface to the lead system 19 and the digital chip 440. For example, a startup/bias-current/reference module 422 contains the power-up signals used to initialize the pacemaker circuit when the battery is first applied. A low battery module 424 detects four voltage levels of the battery voltage for determining the battery status. A case amplifier 426 generates a CASE bias voltage that is used as a reference for the sense and IEGM (intracardiac electrogram) amplifier module 428. The module 428 includes the P-wave amplifier 22 and the R-wave amplifier 24, described above in FIG. 1. A measured data module 430 measures the battery voltage and current and other analog parameters of the pacing system. An ADC and Logic module 432 includes an analog-to-digital converter (ADC) and timing logic that are used to convert the analog signals of the pacemaker to 8-bit digital words. These digital words are then passed to a digital module 434, which module is used to generate all the basic timing and bus control functions as data is passed back and forth between the analog chip 420 and the digital chip 440.

As shown in FIG. 11, it is seen that a Runaway Protection (RAP) circuit oscillator 436 is also coupled to the Digital Module 434. Such oscillator 436 provides an independent time base for limiting the highest pacing rate allowed by the pacemaker. Further coupled to the digital module 434 is the sensor circuit 408. The sensor circuit 40 includes appropriate sensors for sensing activity and other parameters. For example, an O2 sensor circuit 409 may be used in conjunction with the oxygen sensor lead, when used, to measure blood oxygen of the patient. An activity sensor 408 may also be used to sense patient activity as measured, e.g., by an accelerometer. A charge pump circuit 438 generates the output voltages for the stimulation pulses that are delivered to the patient's heart. A network of output switches 439 connects the charge developed by the pump circuit 438 to the output leads at the appropriate time to form the appropriate stimulation pulses.

It is thus seen that the analog chip 420 contains the necessary circuitry to sense and detect atrial or ventricular events, digitize IEGM waveforms, measured data and other various analog signals, and provide such sensed and digitized signals to the digital module 434 for use by the digital chip 440. The charge pump circuit 438 acts as a voltage doubler/tripler for high output pulse capability. The output pulse width is controlled by the output switches 439. The condition of the battery is monitored, and independent Runaway Protection is provided.

Figure 12:
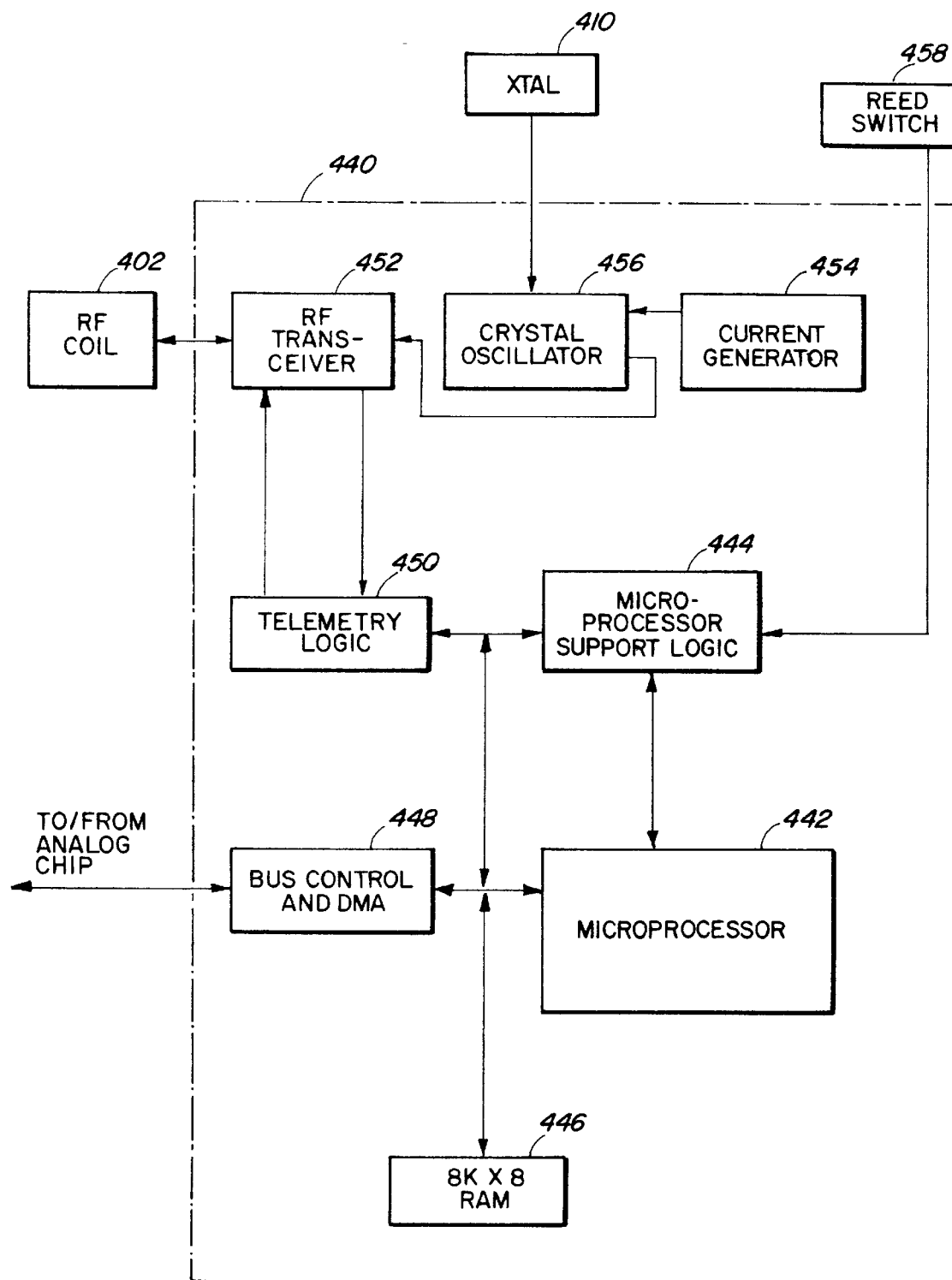
FIG. 12 is a block diagram of the digital chip portion of the pacemaker of FIG. 10, and illustrates the use of a microprocessor to control the operation of the pacemaker.

In FIG. 12, it is seen that the main control element of the pacemaker is a microprocessor 442, which microprocessor is included within the digital chip 440. The digital chip 440 contains all the necessary logic to interface the analog chip 420 with the internal microprocessor 442. The microprocessor 442 includes a basic CPU (central processing unit) and 8K of static RAM (random access memory). In addition, an 8K by 8K RAM 446 is connected to the microprocessor 442 to store data and programs. Microprocessor support logic 444, also coupled to the microprocessor 442, includes interrupt logic, timer logic, noise/sensed event logic, and magnet status logic. A bus controller 448 is further included on the digital chip 440 to provide DMA timing and control of data transfer with the analog chip 420, including logic timing and control of the analog-to-digital converter 432 (FIG. 11) and telemetry data. Telemetry channel logic 450 contains clock logic, IEGM and marker logic, telemetry command protocol logic, telemetry interrupt logic, error checking logic and CPU reset logic. An RF transceiver 452, coupled to the RF coil 402, transmits and receives telemetry data from the external programmer 48 through the telemetry head 49 (see FIG. 10). A crystal oscillator circuit 456, in conjunction with the crystal 410 (external to the digital chip 440) provides the crystal time base of the pacemaker system. A current generator 454 provides the bias currents for the digital chip. A reed switch circuit 458 detects the presence of a magnetic field, which magnetic field is present whenever the telemetry head 49 is in place on the patient's skin above the location where the pacemaker is implanted.

The pacemaker circuitry described in connection with FIGS. 10–12 above provides the basic functions of the pacemaker described in connection with FIG. 1, plus other pacing/sensing functions as are known in the art. For purposes of the present invention, the pacemaker circuitry of FIGS. 10–12 sets the basic timing of the pacing interval, including setting an AV interval and a VA interval. The circuitry also provides for sensing or detecting ventricular events (R-waves) and/or atrial events (P-waves), and for measuring and "learning" the time interval between a sensed or paced atrial event and a conducted ventricular event (R-wave). Such AR/PR time interval, as indicated previously, comprises the natural conduction time of the patient's heart. In accordance with the present invention, the AV interval is initially set to a long value greater than the natural conduction time. The AV interval remains at such long value for so long as AV conduction is present, i.e., for so long as an R-wave is sensed before the timing out of the AV interval. If an R-wave is not sensed before the timing out the long AV interval, then that indicates that AV block is present, and the AV interval is shortened to its shorter value to assure that needed ventricular support is provided. Meanwhile, the natural conduction time, once learned, is saved or stored as a reference value. Such reference value is then used as a standard or reference against which subsequent measured AR intervals are compared to determine if the R-wave that concludes such subsequent AR intervals is a conducted R-wave, which signals the return of AV conduction, or an ectopic, pathologic, or other early R-wave, that does not signal the return of AV conduction.

In some embodiments of the invention, the pacemaker circuitry may include means for measuring the amplitude of a sensed R-wave, and/or examining the morphology of a sensed R-wave, and for comparing such measured or examined amplitude/morphology with previously defined amplitudes and/or morphologies indicative of the presence or absence of AV conduction. Further, timing circuitry may be employed that defines a programmable time window synchronized with the cardiac cycle during which a sensed R-wave suggests the return of AV conduction.

If AV conduction has returned, then the AV interval is reset to its longer value. If AV conduction has not returned, then the AV interval remains at its shorter value. In this way, then, the pacemaker's AV (or PV) interval automatically is set to a longer or shorter value in order to maintain appropriate hemodynamics to maximize cardiac output for a given patient.

It is noted that in addition to the embodiment of the invention illustrated in FIGS. 10–12, still other embodiments of a control system 26 may be utilized. The embodiment described above in FIGS. 10–12 shows a control system and pacemaker configuration that is based on a microprocessor. Another representative microprocessor-based system is described, for example, in U.S. Pat. No. 4,940,052, entitled "Microprocessor Controlled Rate-Responsive Pacemaker Having Automatic Threshold Adjustment," incorporated herein by reference. The control system may also be based on a state machine wherein a set of state registers define the particular state of the pacemaker at any instant in time. As is known in the art, state machines may be realized using dedicated hardware logic circuits, or a suitable processor (programmed-controlled circuit) to simulate such dedicated hardware logic circuits. However implemented, the results are the same—the state of the pacemaker is defined at any instant of time by the pacemaker logic and sensed events which transpire or fail to transpire, such as the sensing of an R-wave, or the timing out of a timer. A description of basic state machine operation may be found, e.g., in U.S. Pat. No. 4,712,555. Reference is also made to U.S. Pat. No. 4,788,980, wherein the various timing intervals used within the pacemaker and their interrelationship are more thoroughly described; and U.S. Pat. No. 4,944,298, wherein an atrial-rate based programmable pacemaker is described, including a thorough description of the operation of the state logic used to control such a pacemaker. The '555, '980 and '298 patents are also incorporated herein by reference.

The details of the control system 26, whether based on a microprocessor, state machine, or other type of control devices, or simulated control devices, are not critical to an understanding or implementation of the present invention, and hence are not presented herein. Such details may be found in the referenced applications and patents, if desired.

All that is important for purposes of this embodiment of the present invention is that the control system of the pacemaker be capable, in conjunction with other pacemaker circuitry, of: (1) measuring the AR interval defined as a time interval between an atrial event (i.e., the generation of an A-pulse or the sensing of a P-wave) and a sensed R-wave; (2) averaging the AR interval over a prescribed number of cardiac cycles to define a "learned" AR interval, the "learned" AR interval corresponding to a natural conduction time of the heart; (3) determining whether an R-wave is naturally conducted by comparing the AR interval with the "learned" AR interval; (4) shortening the AV interval by a prescribed amount when AV conduction is not present, i.e., when AV block occurs; and (5) setting the AV interval to a long or short value as a function of whether AV conduction has returned or not, respectively.

The control system should also be capable of regularly checking, whenever the short AV interval is being used, to determine if AV conduction has returned by, e.g., (a) systematically increasing the AV interval in small increments up to its longer value, (b) looking for the occurrence an R-wave before the timing out of the AV interval, (c) measuring the AR interval associated with any R-wave that does occur before the timing out of the AV interval, and (d) testing the measured AR interval of any R-wave that does occur against the "learned" AR interval to determine if such R-wave represents the return of AV conduction;

The control system should also be capable, in conjunction with appropriate sensor circuitry, of adjusting the long and short values of the AR interval as a function of the sensor-indicated rate signal.

Note that the measurement or learning of the AR interval can be made in conventional manner, and may involve an averaging of the AR interval over several cardiac cycles, or other computation or estimation of the AR interval as is known in the art. Once the AR interval has been measured, or otherwise learned, the pacemaker then sets its AV (or PV) interval to a long or short value as described above.

For other embodiments of the invention, the control system should be capable, in conjunction with other pacemaker circuitry, of: (1) setting the AV interval to a programmed initial value; (2) sensing whether an R-wave occurs during such AV interval, and if not (3) issuing a V-pulse at the conclusion of the AV interval and then shortening the AV interval to a shorter value; (4) maintaining the AV interval at its shorter value for a prescribed number of cardiac cycles or for a prescribed time; (5) periodically (or in accordance with a prescribed schedule) scanning for the return of AV conduction, and if AV conduction returns (6) returning the AV interval to its initial (longer) value. A feature of the invention is that the control system of such embodiments, in conjunction with other pacemaker circuitry, is configured to readily recognize that the return of AV conduction. AV conduction may be verified, e.g., by simply monitoring the ventricular channel for the occurrence of one or more R-waves, and monitoring or measuring such R-waves (e.g., by measuring/monitoring time of occurrence, number of consecutive occurrences, amplitude, and/or morphology) to determine if the sensed R-waves are indicative, or consistent with, the presence of AV conduction.

Figure 5:
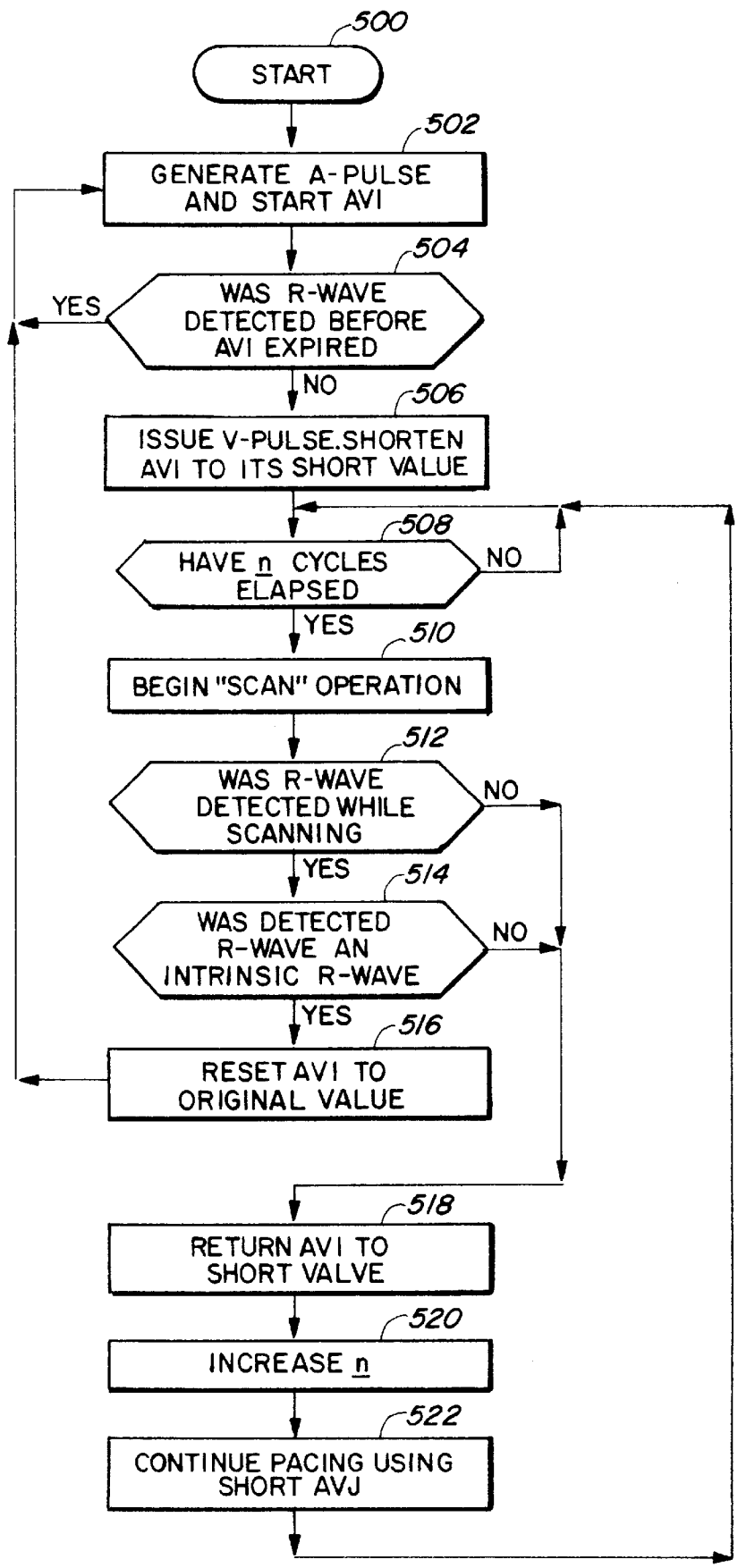
FIG. 5 is a flow chart of the steps traversed by the electronic pacemaker of FIG. 1 in order to initiate and terminate the ventricular support response as described in reference to FIGS. 2, 3 and 4.

In FIG. 5, the above-described process—of determining the natural conduction time (AR interval), and setting the AV (or PV) interval to a short or long value as a function of whether AV conduction is present or not—is illustrated in a high level flow diagram. In FIG. 5, each main step of the process or sequence is shown as a "block" or "box," with each block having a reference numeral assigned thereto to aid in the explanation thereof. Such flowchart is particularly helpful when the invention is implemented using a microprocessor, or equivalent processing device, that follows a stored program, with the flowchart representing the stored program that is used by such processor.

Figure 2:
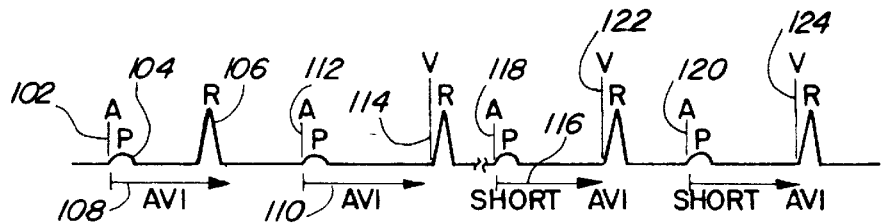
FIG. 2 is an illustration of an exemplary timing/event diagram that depicts the cardiac and pacemaker events that transpire when the pacemaker of FIG. 1 detects the need for ventricular support pacing.
Figure 3:
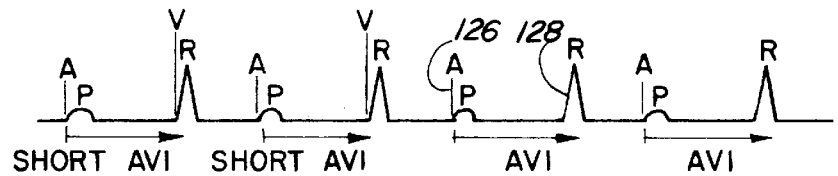
FIG. 3 is an illustration of an exemplary timing/waveform diagram as in FIG. 2 that depicts the cardiac and pacemaker events that transpire when the pacemaker of FIG. 1 carries out a conducted R-wave "scan" operation and determines that ventricular support pacing is no longer needed.
Figure 4:
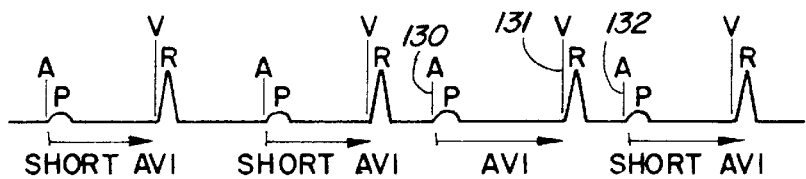
FIG. 4 is an illustration of an exemplary timing/waveform diagram as in FIG. 2 that depicts the cardiac and pacemaker events that transpire when the pacemaker of FIG. 1 carries out a conducted R-wave "scan" operation and determines that ventricular support pacing continues to be needed.

Before describing the flow diagram of FIG. 5, however, it will be helpful to explain the invention in terms of the timing/event diagrams of FIGS. 2–4. Such timing/event diagrams illustrate the relevant cardiac/pacemaker "events" that occur over a sequence of several cardiac cycles, including the occurrence of P-waves, R-waves, the generation of A-pulses and V-pulses, and whether the pacemaker is using a long or short AV interval.

In FIG. 2, an illustration of a timing diagram is shown that depicts the main cardiac/pacemaker events that occur when the electronic pacemaker 10 (FIG. 1) is operating in accordance with functional AAI modality and detects, in accordance with the present invention, the need for ventricular support pacing. As shown in FIG. 2, a first A-pulse 102 is followed by a first P-wave 104 and a first (conducted) R-wave 106. The AV interval (AVI) is also depicted as a line 108 beginning at the first A-pulse 102 and terminating with an arrowhead a prescribed period of time (e.g., 300 ms) following the first A-pulse. In practice, the original AVI may be a fixed value, hard coded into the electronic pacemaker; may be a value that is programmed transcutaneously into the electronic pacemaker using the external programmer, or may be a value that is adapted by the electronic pacemaker, e.g., as a function of a sensor-indicated rate. A dot interposed in the AVI line 108 before the arrowhead signifies the occurrence of the first R-wave 106 before the termination of the AVI. In practice, such occurrence indicates to the electronic pacemaker 10 that ventricular support is not needed. Similar notation is used throughout FIGS. 2–4 and 6–9.

Note that throughout the timing/event diagrams described herein, it is assumed that atrial pacing is required, and therefore an A-pulse is shown at the beginning of each cardiac cycle. It will be understood, however, by one skilled in the art, that the teachings herein are equally applicable to situations wherein a natural, spontaneous P-wave signal begins each cardiac cycle. Thus, reference to an A-pulse within the descriptions presented herein should be understood to apply to any atrial event, to a naturally occurring P-wave or an A-pulse.

As shown in FIG. 2, a second AVI 110 is initiated in response to a second A-pulse 112. The AVI 110 expires before the occurrence of a conducted R-wave. In response to such expiration, a first V-pulse 114 is generated, which is followed by a second (induced) R-wave. Thus, in accordance with the teachings of the present invention, the expiration of the AVI 110 initiates a ventricular support response within the electronic pacemaker. The ventricular support response includes substituting a "short" AVI 116 for the original AVI 110. The short AVI 116 may be, e.g., 200 ms in duration. In practice, the short AVI, like the original (or longer) AVI, may be a fixed value, may be a value that is programmable transcutaneously using e.g., the external programmer 48, or may be a value that is adapted by the pacemaker, e.g., as a function of a sensor-indicated rate. Advantageously, such short AVI improves the hemodynamic efficiency of the heart, whenever ventricular support pacing is required, over the relative inefficiency that would result if the longer AVI were used. The original (or longer) AVI, however, reduces the occurrence of unnecessary ventricular stimulation (V-pulses). Thus, in this way, the present invention dramatically improves upon heretofore known approaches that use ventricular support pacing in, e.g., a DDD modality pacemaker functioning in the AR pacing state due to a long programmed AVI, i.e., a pacemaker that triggers the AVI upon the generation of an A-pulse or the detection of a P-wave.

In FIG. 2, it is seen that the short AVI is initiated in response to third A-pulse 118 and a fourth A-pulse 120. V-pulses 122 and 124 are generated in response to each of these short AVI's expiring (timing out) before the occurrence of a conducted R-wave. The above-described ventricular support response, utilizing the short AVI, continues until the electronic pacemaker determines that such support is no longer needed. The determination that ventricular support is no longer needed is made as depicted in FIGS. 3 and 4.

In FIG. 3, an exemplary timing/event diagram is illustrated to depict the events that occur as the electronic pacemaker 10 (FIG. 1) carries out an R-wave "scan" operation. Such "scan" operation is performed to determine whether the ventricular support response (described in FIG. 2) continues to be needed. As can be seen in FIG. 3, the short AVI is presumed to be present, and is initiated in response to first and second A-pulses. In practice, the first and second A-pulses (in FIGS. 3 and 4) represent the last two A-pulses in a series of A-pulses following the initiation of the ventricular support response. The first two A-pulses in this series are the third and fourth A-pulses 118 and 120 shown in FIG. 2. The first and second A-pulses in FIG. 3 may be, e.g., the ninth and tenth A-pulses in this series. Thus, it is seen that the short AVI, once triggered, continues for a prescribed number of cardiac cycles. The prescribed number of cycles may be relatively low, e.g., ten cardiac cycles, particularly when the short AVI is first triggered after a long period of having used the long AVI. Alternatively, the prescribed number of cycles may be much higher, e.g., 128–512 cardiac cycles. In one embodiment of the invention, a preferred number of cardiac cycles for maintaining the short AVI once triggered is 256.

Following the prescribed number of cardiac cycles, i.e., after the generation of the last A-pulse in the series (i.e., the second A-pulse of FIG. 3), the AVI is returned to its original (long) value in response to the next A-pulse (i.e., A-pulse 126). The purpose of returning the AVI to its original (long) value is to scan for the occurrence of a conducted R-wave. As an alternative to abruptly lengthening the AVI to its longer value, the AVI may be progressively lengthened from its short value to its long value over (e.g., 4–16 cardiac cycles). A cardiac cycle in which the original AVI is initiated, or in which the AVI is lengthened progressively, following a series of cardiac cycles in which the short AVI is used, is referred to herein as a "scan" cycle. In this context the original AVI, or progressively lengthened AVI, is used by the electronic pacemaker to "scan" for the recurrence of a conducted R-wave after the ventricular support response has been initiated for a prescribed period.

Thus, as shown in FIG. 3, when the AVI is abruptly increased to its original value following A-pulse 126, a conducted R-wave 128 occurs before the expiration of the lengthened AVI. The occurrence of R-wave 128, once verified as a conducted R-wave (as opposed to an ectopic, pathologic, or other early R-wave), indicates that AV conduction has returned and that the ventricular support response is no longer needed. Hence, the ventricular support response is terminated, which means that the longer (original) AVI is used from that point forward. The longer AVI continues to be used until such time as a new determination is made that AV block has returned (as described in reference to FIG. 2).

In FIG. 4, an exemplary timing diagram is illustrated to show the events that occur when the pacemaker 10 (FIG. 1) carries out an R-wave "scan" and determines that the ventricular support response (described in FIG. 2) continues to be needed. As can be seen in FIG. 4, the short AVI is presumed to be present. As with FIG. 3, the first and second A-pulses of FIG. 4 represent the last two A-pulses in the series of A-pulses following the initiation of the ventricular support response. Following the generation of the last A-pulse of the specified series, the AVI following the next A-pulse 130 is returned to its original (or longer) value in order to "scan" for a conducted R-wave. When such a "scan" is performed, unlike in the situation shown in FIG. 3, no conducted R-wave occurs before the expiration of the longer AVI. The lack of a conducted R-wave indicates that the ventricular support response continues to be needed. Hence, a V-pulse 131 is generated at the conclusion of the longer AVI, and the next AVI, following A-pulse 132, is made short. The short AVI that follows the A-pulse 132 continues to be used following each subsequent A-pulse until it is again time to perform a "scan" operation in order to look for conducted R-waves. This process continues until a conducted R-wave is detected during the original (longer) AVI. In this way, the invention periodically "scans" for the resumption of conducted ventricular cardiac activity, while maintaining improved hemodynamic efficiency in the heart during the intervening series of cardiac cycles. The ventricular support response is terminated only when a conducted R-wave is detected during a scan cycle.

A key component of the invention described thus far relates to detecting or discerning a conducted R-wave that occurs during a "scan" (long AVI) operation, from an R-wave that is not a conducted R-wave, e.g., an ectopic or pathologic R-wave. One technique used by the invention to discriminate a conducted R-wave from a nonconducted R-wave is described below in connection with FIGS. 6–9. Other techniques, in conjunction with or in addition to that shown in FIGS. 6–9, may also be used in discerning a conducted R-wave form a nonconducted R-wave, as also explained below.

In FIG. 5, a flow chart is shown of the main steps traversed by the control system 26 of the electronic pacemaker 10 (FIG. 1) in order to initiate and terminate a ventricular support response (as described above in connection with FIGS. 2–4). After carrying out an appropriate initialization routine (such as are commonly known in the art of, e.g., microprocessors and state-machines), the electronic pacemaker 10 (FIG. 1) starts its operation (block 500) by setting the AVI to a long value (block 501). The AVI will be initiated in response to each atrial event (where an "atrial event" comprises either an A-pulse generated by the electronic pacemaker, as illustrated, for example, by the A-pulses 102 and 112 of FIG. 2; or a naturally occurring P-wave). The electronic pacemaker also sets n to its low value, e.g., 4–16 (block 502), as will be described in more detail below.

Once initialized, the electronic pacemaker then issues an A-pulse and begins the AVI (block 503). A determination is then made as to whether an R-wave occurs following the A-pulse and before the expiration of the AVI (block 504). In the event an R-wave is so detected (YES branch of block 504), the AVI interval is kept at its long value (block 501), n is kept at its low value (block 502), the next A-pulse is generated (at the appropriate time) and the next AVI begins (block 503). This process (blocks 501, 502, 503 and 504) repeats for so long as an R-wave is detected before the expiration of the long AVI.

Should an R-wave not be detected (NO branch of block 504) before the expiration of the AVI, indicating that at least first degree AV block has occurred, then a V-pulse is generated, and the AVI is shortened to its short value (block 506). Pacing then continues using the short AVI for n cardiac cycles (blocks 522, 503, 504, 506, 508, etc.). That is, in accordance with the programmed dual-chamber operation, an A-pulse is generated, followed by the short AVI. A V-pulse is generated at the end of the short AVI. After a prescribed atrial escape interval, another A-pulse is generated, and the process continues. Should an R-wave be detected before the expiration of a short AVI, then such R-wave inhibits the generation of a V-pulse at the end of the AVI, but has no other effect.

After n pacing cycles have elapsed using the short AVI (block 508), where n is a programmable number having a first-pass value of (e.g., 4–16 cycles, or more), then a "scan" operation begins (block 510). It is the purpose of the "scan" operation to determine if AV conduction has returned. The scan operation commences by restoring the AVI to its original (long) AVI (block 510), either in one cycle or progressively over several cycles. If an R-wave is detected while "scanning," i.e., during a lengthened AVI (YES branch of block 512), then a determination is made (as explained below) as to whether such detected R-wave is a conducted R-wave (block 514). If so (YES branch of block 514), then the AVI is returned to its original (long) value (block 501), n is set at its low value (block 502), and normal pacing resumes using such long AVI (blocks 501, 502, 503, 504 et seq.).

If an R-wave is not detected while scanning (NO branch of block 512), or if a detected R-wave is not confirmed as a conducted R-wave (NO branch of block 514), then the AVI is set to its short value (block 518), the value of n is changed to an appropriate second-pass value, e.g., 64 to 512, and pacing continues with ventricular support using such short AVI (block 522) for the prescribed number n of cycles (block 508). Note that the number n of cardiac cycles that must elapse using the short AVI the first time AV block is detected is not necessarily the same as the number of cycles that must elapse using the short AVI once a "scan" operation has been invoked but no conducted R-waves were detected. Thus, for example, before invoking the "scan" operation, n may be a relatively small number, e.g., 4–16. After a "scan" operation, however, n may be a relatively large number, e.g., 128–256. In this manner, once a sustained AV block has been confirmed, and reconfirmed, a significant number of cardiac cycles, and hence a non-trivial amount of time, must transpire before an additional scan operation is invoked. (In the description above, the suggested values for n are usually stated in terms of powers of two, $2^i$, for purposes of implementing in a digital counter, however, any convenient low and high value may be chosen.)

One of the steps in the process mentioned above (at block 514) relates to confirming whether an R-wave was a conducted R-wave. Such confirmation is performed in order to assure that AV conduction has returned for more than just a transitory period of time. Typically, such confirmation is made by repeating the scan operation for a prescribed number of cycles, e.g., 4–8 cycles. If an R-wave consistently occurs over 4–8 consecutive scan cycles (i.e., cycles with a longer AVI), then that provides a good indication that AV conduction has in fact returned. Further, it is noted that, in general, requiring two or three or more (e.g., 4–8) consecutive occurrences of a prescribed event, e.g., the sensing of an R-wave, or the generation of a V-pulse, is one technique that may be used by the invention to confirm or verify that it is an appropriate time to change the AV interval (from long to short, or from short to long) or to take other action.

One of the reasons for confirming that an R-wave is in fact a conducted R-wave is to avoid having ectopic, pathologic, or other early R-waves (e.g., as occur during a PVC) from being falsely classified as conducted R-waves. That is, when conducted R-waves occur regularly, then such regularity signals the return of AV conduction. The return of AV conduction, in turn, means that the pacemaker should respond by ceasing any ventricular support and lengthening the AVI back to its original (long) value. If an early (nonconducted) R-wave occurs, such R-wave does not signal the return of AV conduction. Hence, it is important that such early R-waves be distinguished from conducted R-waves so that the pacemaker can respond by either lengthening or not lengthening the AVI.

The present invention, in accordance with one embodiment thereof, distinguishes conducted R-waves from nonconducted R-waves by measuring and "learning" the AR interval, or natural conduction time of the patient. Then, when an R-wave is subsequently detected, the AR time interval associated with the detected R-wave is compared with the "learned" natural conduction time. If the R-wave is a conducted R-wave that evidences the return of AV conduction, the AR time interval associated with the detected R-wave will be roughly the same as the previously "learned" natural conduction time, e.g., within ±10–20%. If the R-wave is not a conducted R-wave, however, but is an early R-wave, then the AR time interval associated with the detected R-wave will be significantly different than the previously "learned" natural conduction time. Thus, by simply "learning" the natural conduction time over a suitable number of cardiac cycles, and then using such learned natural conduction time as a reference against which subsequent AR intervals can be compared, a determination can be made as to whether the R-wave associated with the subsequent AR interval is a conducted R-wave or not.

Using the learned time duration of the natural conduction time (AR interval) as a reference against which subsequent AR intervals can be compared is just one way that the present invention can distinguish between conducted R-waves and nonconducted R-waves. Other techniques that may be used include monitoring the timing of when a sensed R-wave occurs within the cardiac cycle. Such monitoring may involve, e.g., specifying (programming) a time window or time threshold within the cardiac cycle that defines a time boundary for distinguishing conducted R-waves from nonconducted R-waves. If an R-wave occurs within the time window or after the time threshold, it is presumed to be a conducted R-wave. If it does not, it is presumed to be a nonconducted R-wave. Such approach is similar to that described above (relative to measuring the natural conduction time and thereafter using such measured natural conduction time as a reference against which subsequent AR intervals can be compared) except that a measurement—at least a measurement made by the pacemaker circuitry—of the AR interval is not necessarily required. Rather, a physician or other medical personnel (or even the pacemaker manufacturer) need only estimate (e.g., from prior experience, or from examining an EKG of the patient or from a sample of patients) what an appropriate "time window" might be for the patient, and then program or set such value into the pacemaker circuits.

Yet another technique for verifying conducted R-waves from nonconducted R-waves that may be used by the present invention is to require that at least a prescribed number of R-waves, e.g., at least two, occur in consecutive cardiac cycles at approximately the same time within the cardiac cycle, and more particularly within the AV interval of the cardiac cycle. If the prescribed number of R-waves repeat at approximately the same time within the AV interval of consecutive cardiac cycles, that is a usually a good indication that the R-waves are conducted R-waves. This is because nonconducted R-waves (at least those that occur after an atrial event within the time window normally set for an AV interval), tend to be more erratic and less repetitive than do conducted R-waves. Thus, if a nonconducted R-wave occurs during the AV interval, the chances are that it will not repeat, particularly over two, three, or four or more consecutive cardiac cycles.

Yet another technique that may be used in some embodiments of the invention to discern conducted R-waves from nonconducted R-waves involves measuring the amplitude of the R-wave. Ectopic and pathologic R-waves tend to be smaller in amplitude than do conducted R-waves. Hence, if the amplitude of the sensed R-wave exceeds a prescribed threshold, then that provides some indication that the sensed R-wave is in fact a conducted R-wave.

A related technique that may be used in other embodiments of the invention to discern conducted R-waves from nonconducted R-waves relates to examining the morphology (shape) of the sensed R-wave and comparing such morphology to the morphology of known conducted R-waves. This technique thus relies on the fact that conducted R-waves are characterized by distinct, recognizable, features, (e.g., in terms of their slope, amplitude, width, etc.) from nonconducted R-waves. Thus, by detecting such characteristics, or by capturing the entire "image" of the sensed R-wave, and by comparing such captured information to corresponding information previously obtained or defined from known conducted R-waves, it is possible to classify the sensed R-wave as a conducted R-wave or a nonconducted R-wave. Circuitry for examining the morphology of an R-wave is disclosed, e.g., in U.S. patent application Ser. No. 08/310,688, filed Sep. 22, 1994, which application is incorporated herein by reference.

Figure 6:
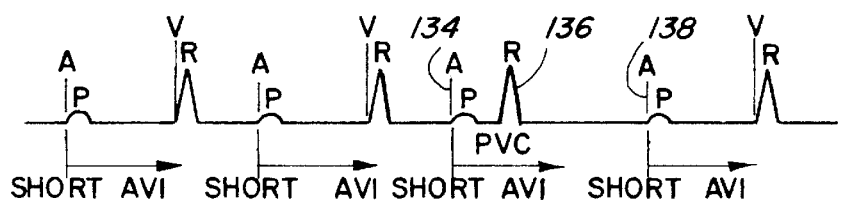
FIG. 6 is an illustration of an exemplary timing/waveform diagram as in FIGS. 2–4 that depicts the cardiac and pacemaker events that transpire when the pacemaker of FIG. 1 detects a premature ventricular contraction (PVC)

In FIG. 6, a timing/event diagram is shown (similar to those of FIGS. 3 and 4) that depicts an alternative technique for detecting a premature ventricular contraction (PVC) during a time when the short AVI has been invoked. As represented in FIG. 6, first and second A-pulses, generated by the electronic pacemaker, each initiate the short AVI. At the end of each short AVI, the electronic pacemaker generates a V-pulse. Following a third A-pulse 134, an R-wave 136 is detected. Because the R-wave 136 is detected during the short AVI, however, as opposed to being detected during the original (long) AVI, such R-wave is assumed to be caused by a premature ventricular contraction (PVC), i.e., a late cycle ventricular ectopic beat or a junctional beat, and not a conducted R-wave in response to an atrial event, either a naturally occurring P-wave or an A-pulse. The electronic pacemaker, having determined that the detected R-wave 136 is due to a PVC, suppresses generation of a V-pulse following the short AVI, but does not restore the original (long) AVI. That is, the electronic pacemaker does not cease the ventricular support response. Instead, the electronic pacemaker continues to carry out the ventricular support response, including initiating the short AVI following a fourth A-pulse 138 (and subsequent A-pulses in the above-described series of A-pulses), and pacing the ventricle (by generating a V-pulse) at the end of such short AVI.

In reference to FIGS. 3 and 6, in another variation of the invention, the electronic pacemaker 10 detects a conducted R-wave during a "scan" cycle (i.e., a cycle using a longer AVI) only if an R-wave is detected (1) after an A-pulse, (2) before the longer AVI has expired, and (3) after the short AVI has expired. Note, in order to perform the functions of this variation of the invention, both the original (long) AVI and the short AVI must be initiated in response to the A-pulse of the scan cycle and allowed to time out in parallel, thereby defining a time window covering the time interval between the end of the short AVI and the end of the long AVI. (Other techniques may also be used to define an equivalent time window.) Any R-wave detected after the A-pulse of the scan cycle and before the longer AVI expires, but also before the short AVI expires, is assumed to be a PVC. In response to such PVC, the electronic pacemaker 10 suppresses generation of the V-pulse, but continues the ventricular support response, including using the short AVI, following subsequent A-pulses. This variation of the invention not only provides a precise criteria for determining what is and what is not a conducted R-wave, but also assures that the ventricular support response is not terminated in response to a PVC, should a PVC occur after an A-pulse during a "scan" cycle.

Figure 7:
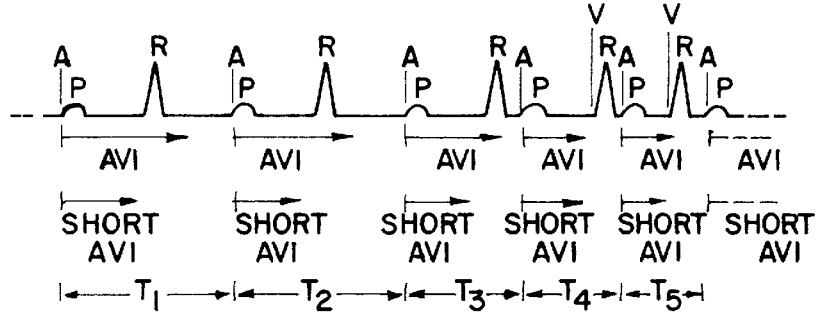
FIG. 7 is an illustration of an exemplary timing/waveform diagram as in FIGS. 2–4 that depicts the cardiac and pacemaker events that transpire when the pacemaker of FIG. 1 detects the need for an increased heart rate.

In FIG. 7, a timing/event diagram is shown that illustrates the cardiac/pacing events that might occur in response to an increased pacing rate initiated by a rate-responsive electronic pacemaker. As represented in FIG. 7, an A-A interval (i.e., the interval of time between A-pulses) decreases with each successive A-pulse, while the AR interval remains about the same. Such a condition could easily occur when the electronic pacemaker 10 detects a need for an increased pacing rate. Problematically, however, such shortening of the A-A interval without a concomitant shortening of the A-R interval could cause an A-pulse to be generated simultaneously with the previous R-wave. This phenomenon, known as AAI(R) pacemaker syndrome, results in the atrium being stimulated to contract against a closed AV valve (closed by the naturally contracting ventricle). Such action results in very poor hemodynamic efficiency. Advantageously, the present invention prevents the occurrence of AAI(R) pacemaker syndrome as described below.

Also shown in FIG. 7 are the original (long) AVI and the short AVI, which are shown for illustration purposes as being initiated in response to each of the A-pulses. The first and second A-A intervals $T_1$, $T_2$ have a duration of about 1 second, and within the first and second A-A intervals the original (long) AVI has a duration of about 300 ms, and the short AVI has a duration of about 200 ms. The third A-A interval $T_3$ has a duration of about 667 ms, and within the third A-A interval the original (long) AVI has a duration of about 275 ms, and the short atrioventricular interval has a duration of about 175 ms. The fourth A-A interval $T_4$ has a duration of about 546 ms, and within the fourth A-A interval the original (long) AVI has a duration of about 250 ms, and the short AVI has a duration of about 150 ms. Finally, the fifth A-A interval $T_5$ has a duration of about 462 ms, and within the fifth A-A interval the original (long) AVI has a duration of about 225 ms, and the short AVI has a duration of about 125 ms. Thus, for the example shown, the original (long) AVI and the short AVI are automatically shortened as the A-A interval is shortened by the rate-responsive electronic pacemaker. As a result of this shortening, the original and short AVI's will not run over into the next cardiac cycle. As a result, the AVI's will expire some time before the generation of the next A-pulse. Expiration of the AVI causes the generation of a V-pulse, which in turn, invokes a ventricular depolarization/contraction, which in turn prevents any subsequent conducted ventricular contraction at the same time as the subsequent generation of an A-pulse.

Advantageously, the changing of the original (long) and short AVI's (referred to herein as rate responsive modulation) assures that, when the A-A interval is shortened through rate-responsive modulation of the electronic pacemaker, the AR interval is also shortened either naturally or through the generation of V-pulses that invoke ventricular contractions. As a result, the possibility of AAI(R) pacemaker syndrome is eliminated.

As seen in FIG. 7, the ventricular support response is still initiated after the fourth A-pulse, even though the original (long) and short AVI's are being shortened. Note further that the "scan" operation described above is preferably suppressed during the rate responsive modulation when the detected cardiac rate exceeds a prescribed threshold, e.g., 90 bpm (beats per minute). This allows the ventricular support response (short AVI) described herein to be initiated, but not terminated, whenever the detected cardiac rate exceeds the prescribed threshold, i.e., whenever the heart rate is elevated. As the heart rate declines below the prescribed threshold, then the "scan" operation may again be invoked to determine if it is appropriate to lengthen the AVI back to its original (long) value.

Figure 8:
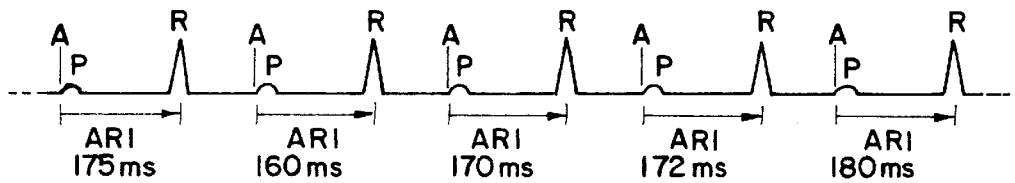
FIG. 8 is an illustration of an exemplary timing/waveform diagram as in FIGS. 2–4 that depicts the cardiac and pacemaker events that transpire as the pacemaker of FIG. 1 "learns" an average AR interval of a patient.

In FIG. 8, an exemplary timing/event diagram is shown that illustrates one way in which an electronic pacemaker "learns" an average AR interval (ARI) of a patient. As illustrated in FIG. 8, the AR interval is measured over a prescribed number of cardiac cycles, e.g., 4–64. After such measurements, or during such measurements, the electronic pacemaker averages the measured AR intervals to determine an average AR interval (AVG ARI). The average AR interval may be updated by the electronic pacemaker 10 during subsequent cardiac cycles during which the AR interval is measured. For the five AR intervals illustrated in FIG. 8, the average AR interval is thus:

$$AVI_{AVE}=(175+180+170+172+180)/5=175.40 \text{ ms.}$$

It should be apparent from the natural conduction times shown in FIG. 8 that, while 175 represents the average AR interval, or average natural conduction time, some R-waves occur before and after this value. Thus, in one embodiment, a prescribed safety margin (e.g., 25 ms) is included with the average AR interval so that all naturally conducted beats are permitted to occur. In this embodiment, any R-wave which occurs during the short AVI and before the expiration of a reference interval (corresponding to the average R-wave minus 25 ms) is considered a nonconducted beat. In an alternative embodiment, illustrated in FIG. 9, the reference interval is thought of as "natural conduction window" which includes a positive and a negative safety margin about the average AR interval. Consequently, a sensed R-wave which occurs outside of a prescribed "natural conduction window," is considered a nonconducted beat.

Besides computing a simple average, as described above, in order to "learn" the natural conduction time, it is noted that other techniques may also be used to learn the AR interval. Such other techniques include, e.g., computing a statistical "mean," "median," "mode," etc. of the measured AR intervals, performing a least-squared analysis of the measured AR intervals, sampling the measured AR intervals, and the like.

As a further option, the AV interval can be "learned," as described above, and then reported to a physician through, e.g., the external programmer 48. The physician may then be given the option to program the pacemaker to use the reported "learned" AV interval, or the option to override the reported "learned" AV interval and substitute another value in its place. In this way, the physician is afforded the opportunity to either use the reported "learned" AV interval or select another AV interval.

Once the AR interval has been "learned," the "learned" value may thereafter be used as a "standard" or "reference" against which subsequent AR intervals may be compared. This process is illustrated in FIG. 9.

In FIG. 9, any R-wave is considered to be a nonconducted beat (e.g., a premature ventricular contraction (PVC)) if it is detected after an A-pulse and outside of a natural conduction window defined as the "learned" AR interval plus or minus a prescribed safety factor. (Note that the safety margin may be a fixed value, e.g., 25 ms, or a programmable value of from, e.g., 0 to 100 ms.) As described previously, when a PVC is detected, it is ignored by the electronic pacemaker 10 for purposes of determining whether the ventricular support response is still needed. The electronic pacemaker does, however, suppress generation of the V-pulse within the cardiac cycle in which the PVC occurs.

As seen in FIG. 9, when the ventricular support response is initiated, the short AVI follows a first A-pulse 156, which short AVI is followed by a first V-pulse 158. The first V-pulse 158 is generated in response to the expiration of the short AVI without an R-wave having been detected. In response to the first V-pulse 158, a first R-wave 159 is evoked. Following the first R-wave 159, a second A-pulse 160 is generated, which is followed by a second R-wave 162. The second R-wave 162 is detected outside of the natural conduction window (NCW), yet before the end of the short AVI. Thus, the second R-wave 162 is presumed to be a nonconducted beat, and is therefore ignored by the electronic pacemaker for purposes of determining whether the ventricular support response is still needed. The nonconducted R-wave 162 does, however, inhibit the generation of a V-pulse at the conclusion of the AVI that follows the second A-pulse 160.

In FIG. 9, a third A-pulse 164 is shown following the second R-wave 162. No R-wave is detected before the expiration of the short AVI that follows the A-pulse 164. Following the second V-pulse 166 a third R-wave, invoked by the V-pulse 166, is shown. A fourth A-pulse 168 follows. The fourth A-pulse 168 again initiates the short AVI, as well as the natural conduction window. Following the fourth A-pulse 168, but before the expiration of the short AVI, a fourth R-wave 170 is detected. Because the R-wave 170 is detected within the natural conduction window, and before the short AVI expires, it is not considered a PVC, but is rather considered a naturally conducted R-wave, and therefore signals that the ventricular support response is no longer needed. Note in this instance that the indication that ventricular support is no longer needed occurs during a cardiac cycle that is not a scan cycle. Because the ventricular support response is no longer needed, the original (long) AVI is initiated in response to a fifth A-pulse 172 that follows the R-wave 170, along with the natural conduction window. A fifth R-wave 174 follows the A-pulse 172 within the natural conduction window, and before the end of the original (long) AVI. The occurrence of the R-wave 174 within this window indicates that the ventricular support response remains unneeded.

As described above, it is seen that the invention is able to detect whether there is a continued need for the ventricular support response, while accurately distinguishing between PVC'S, which do not signal the need to end the ventricular support response, and conducted R-waves, which do signal that the ventricular support response may be ended.

It is noted that thus far, the invention has been described primarily in terms of atrial-based pacing. As is known in the art, dual-chamber pacing may be either atrial based or ventricular based. In atrial-based pacing, the occurrence of an atrial event starts the appropriate timers that define the duration of the basic cardiac cycle, or A-A interval (which A-A interval includes the time interval from an A-pulse to an A-pulse, or from a P-wave to an A-pulse). The A/P-A interval includes the AV or PV interval and an atrial escape interval, AEI, both of which are keyed off of, or start, upon the occurrence of an atrial event, i.e., either the sensing of a P-wave or the generation of an A-pulse. In ventricular-based pacing, in contrast, the basic pacing cycle, or A-A interval, includes the AV interval followed by a VA interval. The AV interval begins upon the occurrence of an atrial event, either a P-wave or an A-pulse. The VA interval begins upon the occurrence of a ventricular event, either an R-wave before the timing out of the AV interval, or the generation of a V-pulse upon the timing out of the AV interval. Thus, when an R-wave occurs, the VA interval begins sooner in the cardiac cycle than it would have had the R-wave not occurred, and the basic A-A interval that defines the basic cardiac cycle is made shorter.

In some instances, where ventricular-based pacing is employed, it is desirable to prevent the A-A interval from being made shorter. Such is accomplished by adding to the VA interval the same amount of time by which the AV interval is shortened when the AVI is switched from a long AVI to a short AVI. That is, if the AVI is shortened by an amount D, then the VA interval is lengthened by the same amount D so as to maintain the same basic time for the A-A interval. Similarly, when operating in a ventricular-based pacing mode, and if the AVI is lengthened by an amount D, then the VA interval is shortened by the same amount D so as to maintain the same basic time for the A-A interval.

When operating in an atrial-based pacing mode, such as the functional AAI pacing mode, there is no need to adjust any timing intervals because both the AV interval and AEI are keyed off of an atrial event and timer.

Turning next to FIGS. 13 and 14, a specific example is shown of the present invention as applied to atrial based timing (FIG. 13) and ventricular based timing (FIG. 14). In both examples, it is assumed that the basic rate of the pacemaker has been set to 60 ppm (pulses per minute), corresponding to a basic pacing rate interval of 1000 msec. It is further assumed that the programmed value of AVI has been set to 150 msec, and that the hysteresis delta (sometimes referred to as the hysteresis interval) has been set to a +100 msec. Note that with the hysteresis delta set to a positive value, that such positive value is added to the programmed AVI in order to define the long AVI used by the present invention when ventricular support is not anticipated as being needed, i.e., when conductive R-waves are anticipated to be present. Thus, the long AVI interval used in the example shown in FIGS. 13 and 14 is 250 msec, while the short AVI interval is 150 msec.

The basic hysteresis technique illustrated in the examples shown in FIGS. 13 and 14 is that if conduction is detected during the programmed AVI (i.e., if a conducted R-wave is sensed that signals the end of an AR or PR interval), then a new AVI, $AVI_N$, is established that is equal to the programmed AVI plus the hysteresis delta, or $AVI_N = AVI +$ Hysteresis Delta=150+100=250 msec. When loss of conduction is detected, (i.e., if no R-wave occurs during $AVI_N$, thereby forcing the pacemaker circuits to issue a V-pulse at the conclusion of $AVI_N$), that is, upon the first PV or AV interval when using $AVI_N$, then $AVI_N$ is canceled, and AV interval returns to its programmed value, AVI. Thus, the AV interval is set to its new (long) value when conduction is detected, and returns to is programmed (short) value when loss of conduction is present. Should 255 consecutive PV or AV intervals occur without conduction being sensed, then a long AVI is established in order to scan for, or unmask, the presence of intrinsic conduction.

This unmasking process is illustrated in FIG. 13. That is, the V-pulse 302 in FIG. 13 represents the end of the 254th AV interval without an R-wave having been sensed. The V-pulse 304 thus represents the end of the 255th AV interval without an R-wave having been sensed. Accordingly, in accordance with the basic unmasking or scanning technique employed by the example of the invention shown in FIG. 13, the AV interval of the 256th cycle, which cycle begins with A-pulse 306, is extended to 250 msec. Such extension uncovers R-wave 308. Once R-wave 308 is confirmed as a conducted R-wave, which confirmation may be made using any of the techniques previously described (such as requiring that an R-wave 308 be continuously present over at least two consecutive cycles), then the new (long) AV interval, $AVI_N$, takes effect. The long $AVI_N$ remains in effect for so long as continuous AR or PR intervals are present, i.e., for so long as R-wave continue to be sensed. As soon as an R-wave fails to be sensed, as evidenced e.g., by the timing out of the AV/PV interval and the generation of a V-pulse 310, then the next AV interval for use in the next cardiac cycle is shortened to its programmed (short) value of 150 msec. Such programmed value of AVI is used, in accordance with the example shown in FIG. 13, until conduction returns, or if conduction does not return, for at least another 255 cardiac cycles.

Note for the atrial-based timing example shown in FIG. 13, that the A-to-A interval remains constant at 1000 nsec. This is because the basic pacemaker timing is keyed off of the occurrence of an atrial event, either a P-wave or an A-pulse. Note also, as previously described, that a programmed PV interval (PVI) may be somewhat shorter than the programmed AVI. For example, if the AVI is programmed to 150 msec., then the PVI might be programmed to 125 msec. Such different in programmed PVI from the programmed AVI carries over to the hysteresis values. That is, with a positive hysteresis delta of 100 msec., the long $AVI_N$ is 150 msec., and the long PV interval, $PVI_N$, would be 125+100=225 msec.

The positive hysteresis example illustrated in FIG. 14 is the same as the example shown in FIG. 13, except that ventricular-based timing is used. That is, a V-pulse 320 in FIG. 14 represents the end of the 254th AV interval without an R-wave having been sensed. In ventricular based timing, note that the AV interval is cascaded in series with a VA interval in order to define a basic pacing rate. Thus, as shown in FIG. 14, if the programmed AV interval is set to 150 msec., and if the basic pacing interval is 1000 msec., then the VA interval must be set to 850 msec., so that the sum of the AV interval and the VA interval will equal 1000 msec. Continuing with the example shown in FIG. 14, the V-pulse 322 represents the end of the 255th AV interval without an R-wave having been sensed. Accordingly, in accordance with the basic unmasking technique employed by the example shown in FIG. 14, the AV interval of the 256th cycle, which AV interval begins after the timing out of the preceding VA interval, begins with A-pulse 324 and is extended to 250 msec. Such extension uncovers R-wave 326, which (for purposes of the example shown in FIG. 14) occurs at about 170 msec. into the AV interval. Because ventricular based timing is used, R-wave 326 also defines the starting point for the next VA interval. Thus, it is seen that the 256th cardiac cycle has a duration of 170 msec+850 msec=1020 msec. Once R-wave 326 is confirmed as a conducted R-wave, which confirmation may be made using any of the techniques previously described (such as requiring that a similar R-wave 328 also be present in the next cardiac cycle), then the new (long) AV interval, $AVI_N$, takes effect. The long $AVI_N$ remains in effect for so long as continuous AR or PR intervals are present, i.e., for so long as R-waves continue to be sensed. As soon as an R-wave fails to be sensed, as evidenced e.g., by the timing out of the AV interval and the generation of a V-pulse 330, then the next AV interval for use in the next cardiac cycle is shortened to its programmed (short) value of 150 msec. Such programmed value of AVI is used, in accordance with the example shown in FIG. 14, until conduction returns, or if conduction does not return, for at least another 255 cardiac cycles.

Note for the ventricular-based timing example of FIG. 14, that the A-to-A interval does not remain constant. So long as V-pacing is provided using the programmed AVI, the A-to-A interval remains at 1000 msec. However, when the new AV interval, $AVI_N$, is used, the duration of a given cardiac cycle varies as a function of the time within the $AVI_N$ when an R-wave is sensed. In the example of FIG. 14, when an R-wave occurred at about 170 msec into the $AVI_N$, the A-to-A interval was extended about 20 msec., or to 1020 msec. When an R-wave did not occur during $AVI_N$, causing V-pulse 330 to be generated upon the timing out of the $AVI_N$, then the next A-to-A interval was extended a full 100 msec (the duration of the hysteresis delta) to 1100 nsec.

As described above, it is thus seen that the present invention provides an implantable pacemaker that automatically sets its AV interval to either a long or short value in order to optimize the hemodynamic performance of the patient's heart with which the pacemaker is used. More particularly, it is seen that the invention automatically invokes an AV shortening procedure that shortens the AV interval, e.g., whenever AV block occurs, and that thereafter automatically searches for the return of AV conduction, e.g., in accordance with a prescribed schedule, so that when AV conduction returns the AV interval may be reset to its original (longer) value.

What is claimed is:

1. An improved method of ventricular support in a dual-chamber implantable electronic pacemaker, the electronic pacemaker including timing means for generating timed intervals, sensing means for sensing P-waves and R-waves, and pulse generating means for generating A-pulses and V-pulses, the method comprising:
    (a) initiating a long atrioventricular interval (AVI) in response to a first atrial event, the first atrial event comprising either a stimulated A-pulse or a sensed P-wave;
    (b) detecting whether an R-wave is sensed during the long AVI initiated in response to the first atrial event;
    (c) generating a first V-pulse following the long AVI initiated in response to the first atrial event whenever an R-wave is not sensed during the long AVI;
    (d) initiating a ventricular support response whenever an R-wave is not sensed during the long AVI initiated in response to the first atrial event, the ventricular support response comprising:
        initiating a short AVI in response to a second atrial event, and
        generating a second V-pulse following the short AVI initiated in response to the second atrial event;
    (e) detecting, whenever the ventricular support response is initiated, whether the ventricular support response continues to be needed by scanning for the recurrence of an R-wave, the scanning for the recurrence of an R-wave comprising:
        initiating the long AVI in response to a third atrial event, and
        detecting whether an R-wave is sensed during the long AVI initiated in response to the third atrial event; and
    (f) terminating the ventricular support response whenever an R-wave is sensed during the long AVI initiated in response to the third atrial event.

2. The method of claim 1, comprising repeating steps (a) and (b) each time an R-wave is sensed during the long AVI initiated in response to the first atrial event.

3. The method of claim 1, comprising repeating step (d) at least one time before carrying out the detecting whether the ventricular support response continues to be needed in step (e).

4. The method of claim 3, comprising repeating steps (d) and (e) at least one time whenever an R-wave is not sensed during the long AVI initiated in step (e).

5. The method of claim 1, further comprising repeating steps (a) through (f) upon terminating the ventricular support response in step (f) whenever an R-wave is sensed in step (e) during the long AVI.

6. The method of claim 1, further comprising:
    detecting whether an increased heart rate is needed; and
    shortening the long AVI and the short AVI whenever an increased heart rate is needed.

7. The method of claim 1, further comprising:
    detecting whether an increased heart rate is needed;
    determining, whenever an increased heart rate is needed, a magnitude of the increased heart rate; and
    suspending the scanning of step (e) whenever the magnitude of the increased heart rate exceeds a prescribed threshold rate.

8. The method of claim 1, further comprising:
    measuring a prescribed number of AR intervals over a prescribed number of cardiac cycles;
    determining an average AR interval of the AR intervals measured over the prescribed number of cardiac cycles;
    initiating a reference time interval no greater than the average AR interval in response to the first and third atrial events;
    ignoring, in steps (c) and (d), any R-wave sensed in step (b) whenever the R-wave sensed in step (b) is sensed during the reference time interval; and
    ignoring, in step (f), any R-wave sensed in step (e) whenever the R-wave sensed step (e) is sensed during the reference time interval.

9. The method of claim 8, further comprising:
    detecting, before generating the second V-pulse referenced in step (e), whether an R-wave was sensed during the short AVI initiated in response to the second atrial event; and
    generating the second V-pulse in step (e) only when an R-wave is not sensed during the short AVI initiated, in step (e).

10. The method of claim 9, further comprising:
    initiating the reference time interval in response to the second atrial event; and
    terminating the ventricular support response whenever an R-wave is sensed during the short AVI initiated in response to the third atrial event providing that such R-wave is not sensed during the reference time interval initiated in response to the second atrial event.

11. The method of claim 1, further comprising:
    learning a reference AR interval as a function of AR intervals measured over the prescribed number of cardiac cycles;
    transmitting information indicative of the learned reference AR interval from the implantable electronic pacemaker to an external receiver;
    transmitting confirmation information from the external transmitter to the implantable electronic pacemaker indicating that the reference AR interval has been confirmed;

initiating the reference AR interval in response to the first and third atrial events whenever the average AR interval has been confirmed;

ignoring the R-wave sensed in step (b) whenever the R-wave is sensed during the reference AR interval initiated in response to the first atrial event and the reference AR interval has been confirmed; and ignoring the R-wave sensed in step (e) whenever the R-wave is sensed during the reference AR interval initiated in response to the third atrial event and the reference AR interval has been confirmed.

12. The method of claim 11, further comprising:

transmitting information to the implantable electronic pacemaker from the external transmitter indicative of an alternative AR interval whenever the reference AR interval is not confirmed;

initiating the alternative AR interval in response to the first and third atrial events whenever the average AR interval is not confirmed;

ignoring the R-wave sensed in step (b) whenever the R-wave is sensed during the alternative AR interval and the reference AR interval is not confirmed; and ignoring the R-wave sensed in step (e) whenever the R-wave is sensed during the alternative AR interval and the reference AR interval is not confirmed.

* * * * *